(12) United States Patent
Siu et al.

(10) Patent No.: US 12,419,536 B2
(45) Date of Patent: Sep. 23, 2025

(54) METHOD AND APPARATUS FOR ASSESSING RESPIRATORY DISTRESS

(71) Applicant: S&V Siu Associates, LLC, Castro Valley, CA (US)

(72) Inventors: Stanley Chan Siu, Castro Valley, CA (US); Jusson Koo, Milpitas, CA (US); Zachary Andrew Siu, Castro Valley, CA (US)

(*) Notice: Subject to any disclaimer, the term of this patent is extended or adjusted under 35 U.S.C. 154(b) by 1235 days.

(21) Appl. No.: 17/195,109

(22) Filed: Mar. 8, 2021

(65) Prior Publication Data

US 2021/0186371 A1    Jun. 24, 2021

Related U.S. Application Data

(63) Continuation of application No. 15/329,041, filed as application No. PCT/US2015/042465 on Jul. 28, 2015, now Pat. No. 10,939,848.

(60) Provisional application No. 62/085,559, filed on Nov. 30, 2014, provisional application No. 62/029,572, filed on Jul. 28, 2014.

(51) Int. Cl.
| | |
|---|---|
| *A61B 5/08* | (2006.01) |
| *A61B 5/00* | (2006.01) |
| *A61B 5/0205* | (2006.01) |
| *A61B 5/024* | (2006.01) |
| *A61B 5/087* | (2006.01) |
| *A61B 5/1455* | (2006.01) |

(52) U.S. Cl.
CPC ........ *A61B 5/0816* (2013.01); *A61B 5/02416* (2013.01); *A61B 5/08* (2013.01); *A61B 5/0826* (2013.01); *A61B 5/087* (2013.01); *A61B 5/0873* (2013.01); *A61B 5/14551* (2013.01); *A61B 5/7235* (2013.01); *A61B 5/0205* (2013.01)

(58) Field of Classification Search
CPC ..... A61B 5/0816; A61B 5/02416; A61B 5/08; A61B 5/0826; A61B 5/087; A61B 5/7235; A61B 5/0205
See application file for complete search history.

(56) References Cited

U.S. PATENT DOCUMENTS

| | | | | |
|---|---|---|---|---|
| 6,342,039 B1* | 1/2002 | Lynn | ..................... | A61B 17/155 600/323 |
| 6,609,016 B1* | 8/2003 | Lynn | ..................... | G16H 20/40 600/323 |
| 6,723,055 B2* | 4/2004 | Hoffman | ................ | A61B 5/085 600/538 |
| 2004/0044276 A1* | 3/2004 | Arnold | ............... | A61B 5/14551 600/323 |

(Continued)

*Primary Examiner* — Sean P Dougherty
(74) *Attorney, Agent, or Firm* — Matthew A. Pequignot; Pequignot + Myers

(57) ABSTRACT

A method and apparatus are disclosed for assessing a respiratory function from plethysmography data obtainable, for example, from a pulse oximeter. A pulsatile waveform obtained from pleth data is processed to obtain a second waveform extending over multiple respiratory cycles and representing respiration-related variations in a pulse-beat area defined by the pulsatile waveform. The second waveform is analyzed to obtain information indicative of respiratory distress. A respiratory index that provides a good indicator of respiratory distress may be computed based on a magnitude of respiratory peaks in the second waveform. Applications to asthma and sleep apnea are described.

10 Claims, 14 Drawing Sheets

(56) References Cited

U.S. PATENT DOCUMENTS

| | | | |
|---|---|---|---|
| 2004/0143194 A1* | 7/2004 | Kihara | A61B 5/6831 600/534 |
| 2006/0155206 A1* | 7/2006 | Lynn | A61M 16/0051 600/323 |
| 2006/0189872 A1* | 8/2006 | Arnold | A61B 5/0205 600/483 |
| 2007/0191688 A1* | 8/2007 | Lynn | A61B 5/4818 600/300 |
| 2007/0191697 A1* | 8/2007 | Lynn | A61B 5/08 600/323 |
| 2013/0025597 A1* | 1/2013 | Doyle | A61B 5/14551 128/204.23 |
| 2013/0060110 A1* | 3/2013 | Lynn | G16H 20/40 600/324 |
| 2013/0190640 A1* | 7/2013 | Adam | A61B 5/7278 600/538 |
| 2013/0281805 A1* | 10/2013 | Mason | A61B 5/349 600/324 |
| 2015/0165200 A1* | 6/2015 | Arnold | A61N 1/37247 607/42 |

* cited by examiner

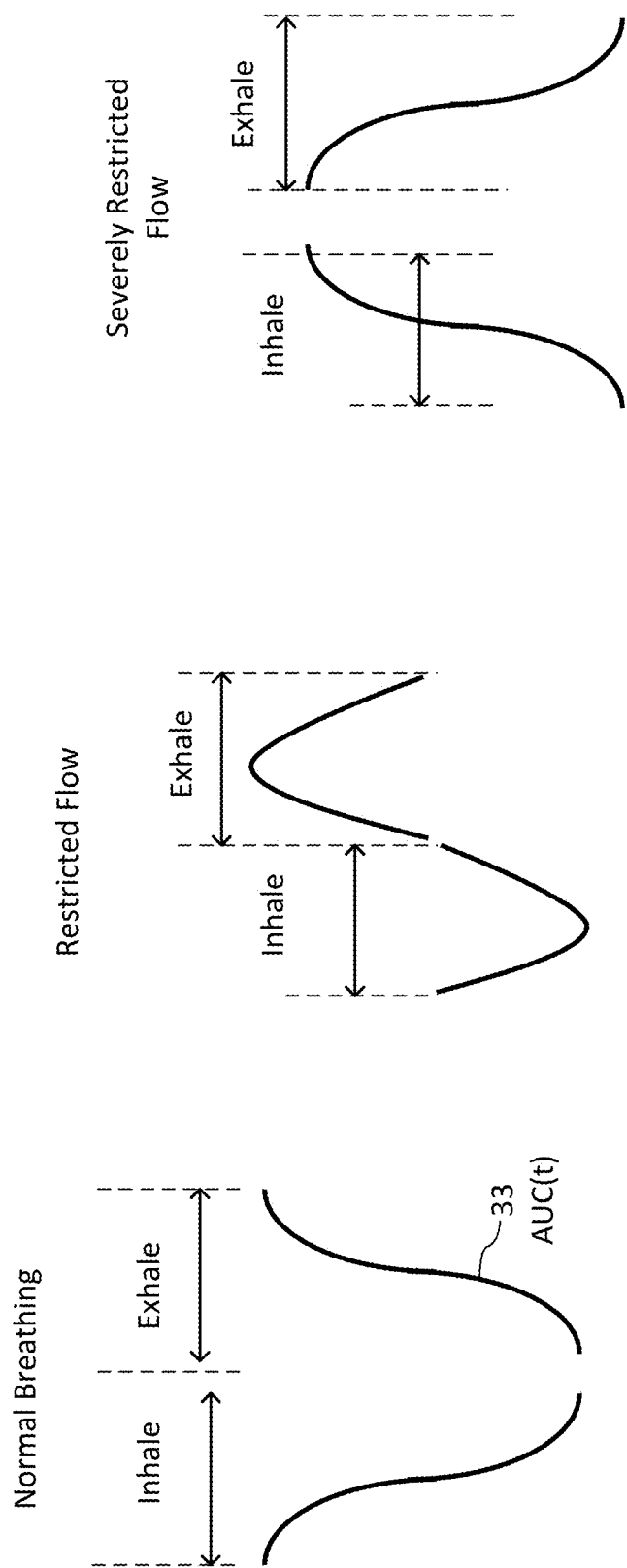

METHOD AND APPARATUS FOR ASSESSING RESPIRATORY DISTRESS

CROSS-REFERENCE TO RELATED APPLICATIONS

The present invention is a continuation application which claims priority from U.S. application Ser. No. 15/329,041 filed Jan. 25, 2017, which is a National Entry from PCT/US2015/42465 filed Jul. 28, 2015 which claims priority from U.S. Provisional Patent Application No. 62/029,572 filed Jul. 28, 2014, entitled "Method and apparatus to measure oximetric respiratory index", and U.S. Provisional Patent Application No. 62/085,559 filed Nov. 30, 2014, entitled "Oximetric respiratory index (ORI) method to detect sleep apnea", all of which are incorporated herein by reference.

TECHNICAL FIELD

The present invention generally relates to measuring and monitoring a physiological parameter or state of a patient, and more particularly relates to systems and methods for assessing respiratory effort or distress in a patient using plethysmography.

BACKGROUND

Optical plethysmography may be used to assess respiratory efforts or distress in a patient by detecting the presence or degree of pulsus paradoxus (PP). The medical term "Pulsus Paradoxus" refers to an abnormally large decrease in systolic arterial blood pressure during inspiration, and a corresponding abnormally large variation in plethysmographic pulse wave amplitude during a respiration cycle. Pulsus paradoxus is indicative of respiratory distress or effort and may be symptomatic of various medical conditions accompanied by respiratory disorders, including but not limited to asthma, sleep apnea, and emphysema. Under normal conditions, variations of the systolic blood pressure over a respiratory cycle typically lie in the range of 2-5 mm Hg. A respiratory disorder may lead to pulsus paradoxus reaching 10 mm Hg or greater. The importance of rapidly detecting and monitoring of pulsus paradoxus for assessing the status of a patient in acute respiratory distress for the purpose of objectively determining the severity of their condition has been long recognized in the art; the National Heart Lung and Blood Institute has recommended that pulsus paradoxus be measured on all asthmatic patients.

An optical plethysmograph is a device that measures changes in blood volume in a part of a patient's body by measuring variations in absorption of red and/or infrared (IR) light by the body part, typically a fingertip, toe, or an earlobe. Changes in the amount of blood in the measurement area, i.e. a vascular bed, cause changes in the absorption of light, which therefore varies in proportion with the amount of blood delivered to that tissue. The plethysmographic signal therefore emulates the arterial pulse pressure waveform and may be used to detect PP.

An often used variant of optical plethysmograph is a pulse oximeter, which uses two or more optical absorption signals obtained at two or more different wavelengths of light, for example about 660 nm (red) and about 940 nm (IR), to measure blood oxygen saturation, or the degree of oxygen saturation of hemoglobin (SpO2). Pulse oximeters typically include a probe that is attached to a patient's appendage and directs light signal pulses from two or more light emitters through the appendage. The intensity of light transmitted by the tissue is monitored by a photodetector. A pulsatile component of the output plethysmographic signal in pulse oximeters reflects the expansion of the arteriolar bed with arterial blood, and provides a basis for monitoring changes in the concentration of the noted blood analytes, oxyhemoglobin and deoxyhemoglobin.

Most of the approaches used heretofore for detecting pulsus paradoxus using a pulse oximeter were based on extracting and measuring frequency component of a plethysmographic signal ("pleth") from the oximeter that relates to respiration, or on measuring changes in pleth waveform height, or on measuring variation of the pleth baseline. It was noted however that these methods may lack in sensitivity and accuracy, and/or may be unreliable, in part because measurements of a single parameter, such as the pleth waveform height, may not be well suited for quantifying PP, which represents a decrease in left ventricular stroke volume ("LVSV") during the inspiratory phase of the respiratory cycle and/or an augmentation of LVSV during the expiratory phase of the respiratory cycle. Furthermore, techniques that do not adequately measure diastolic changes occurring during the cardiac cycle may be inaccurate as they do not adequately take into account contribution of the diastolic changes to pulsus paradoxus. U.S. Pat. Nos. 6,869, 402, 7,044,917, and 7,828,739, which are issued to D. H. Arnold and are incorporated herein by reference, describe a technique for quantifying PP that is based on comparing area under the curve (AUC) for two pulse waveforms extracted from a single pleth signal. Arnold notes that the AUC, being a two-dimensional parameter, may be better suited to quantifying changes in LVSV and related blood flow, and thus to measuring PP, than techniques based on detecting changes in the waveform height or baseline. Although PP estimates (PEP) based on a difference ΔAUC between minimum and maximum AUC values measured over a period of pleth signal was shown to correlate with respiratory effort or distress, the techniques were also found to give frequent false positives and may lack consistency in detecting and quantifying PP, in particular when pulse and/or respiratory rate varies during measurement.

Accordingly, it may be understood that there may be significant problems and shortcomings associated with current solutions and technologies for assessing breathing difficulty and/or effort in a patient, and measuring pulsus paradoxus.

SUMMARY

Accordingly, the present disclosure provides a method and apparatus for assessing a respiratory function of a patient from data indicative of respiration related variations in pulsatile cardiovascular behavior for the patient, such as plethysmography data that may be obtained, for example, from an optical plethysmograph such as a pulse oximeter. A pulsatile waveform obtained from the plethysmography data is processed to obtain a second waveform extending over multiple respiratory cycles and representing respiration-related variations in a pulse-beat area defined by the pulsatile waveform. The second waveform may be analyzed to obtain information indicative of respiratory distress and/or effort. A respiratory index that provides a good indicator of respiratory distress may be computed based on a magnitude of respiratory peaks in the second waveform. Information obtained from the second waveform, including but not limited to the respiratory index, may be used to detect and evaluate respiratory events associated with such medical conditions as asthma and apnea.

One aspect of the present disclosure relates to a method for assessing respiratory distress or respiratory effort in a patient, comprising: a) obtaining plethysmography data defining a pulsatile waveform that extends over a plurality of respiratory cycles and is indicative of respiration related variations in pulsatile cardiovascular behavior for the patient; b) determining, by a processor, a plurality of area under the curve (AUC) values for the pulsatile waveform, the plurality of AUC values defining an AUC waveform extending over the plurality of respiratory cycles and representing time-domain variations in pulse-beat area in the pulsatile waveform due to respiration by the patient; and, c) analyzing, by the processor, the AUC waveform to obtain information indicative of the respiratory distress or respiratory effort in the patient.

According to an aspect of the present disclosure, step c) may include d) identifying respiratory peaks in the AUC waveform related to respiratory cycles for the patient, and e) computing a respiratory index representing a magnitude of one or more of the respiratory peaks in the AUC waveform, wherein e) may comprise computing an area under the curve value AUC2 for a respiratory peak in the AUC waveform as a measure of the magnitude of the time-domain variations in the AUC waveform.

In accordance with an aspect of the present invention, the method may include correlating the respiratory index to a spirometry parameter using a calibration procedure wherein the patient or a tester subject breathes through an air flow restriction device.

Another aspect of the present disclosure relates to an apparatus for assessing respiratory distress in a patient, comprising a computing device, the computer device comprising a processor, a first device interface coupled to the processor and configured to connect to a plethysmograph and to obtain therefrom a pulsatile waveform indicative of pulsatile time-domain variations of cardiovascular pressure of the patient over a plurality of respiratory cycles, and a memory device coupled to the processor and storing instructions executable by the processor. The instructions comprise: instructions (a) for obtaining the pulsatile waveform from the plethysmograph; instructions (b) for determining, from the pulsatile waveform, a AUC waveform representing time-domain variations in pulse-beat area in the pulsatile waveform over the plurality of respiratory cycles, wherein the AUC waveform comprises a time sequence of pulse-beat area values extending in time over the plurality of respiratory cycles; and, instructions (c) for analyzing the AUC waveform to obtain information indicative of the respiratory distress in the patient.

BRIEF DESCRIPTION OF THE DRAWINGS

Embodiments disclosed herein will be described in greater detail with reference to the accompanying drawings which represent preferred embodiments thereof, in which like elements are indicated with like reference numerals, and wherein:

FIGS. 16A, 16B and 16C schematically depict respiratory phase offset of the AUC(t) waveform in dependence on air flow restriction for the patient.

DETAILED DESCRIPTION

In the following description, for purposes of explanation and not limitation, specific details are set forth, such as particular circuits, circuit components, techniques, etc. in order to provide a thorough understanding of the present invention. However, it will be apparent to one skilled in the art that the present invention may be practiced in other embodiments that depart from these specific details. In other instances, detailed descriptions of well-known methods, devices, and circuits are omitted so as not to obscure the description of the present invention.

Note that as used herein, the terms "first", "second" and so forth are not intended to imply sequential ordering, but rather are intended to distinguish one element from another unless explicitly stated. Similarly, sequential labeling of method steps or operations does not imply sequential order of their execution. The term 'waveform' in the context of this specification may refer to any time-domain representation of an oscillatory signal that includes information indicative of the shape of the oscillations in the signal in time domain, and encompasses digital oscillatory signals represented by a time sequence of values. Obtaining a waveform means obtaining data defining the waveform. The term 'patient" may refer to any human or non-human mammal whose physiological data, including plethysmography data, are being collected. 'Plethysmography data' or 'plethysmography signal' may refer to any data or signal containing plethysmography information, i.e. information related to changes in volume of a part of a patient body, typically due to changes in the blood flow.

Figure 1:
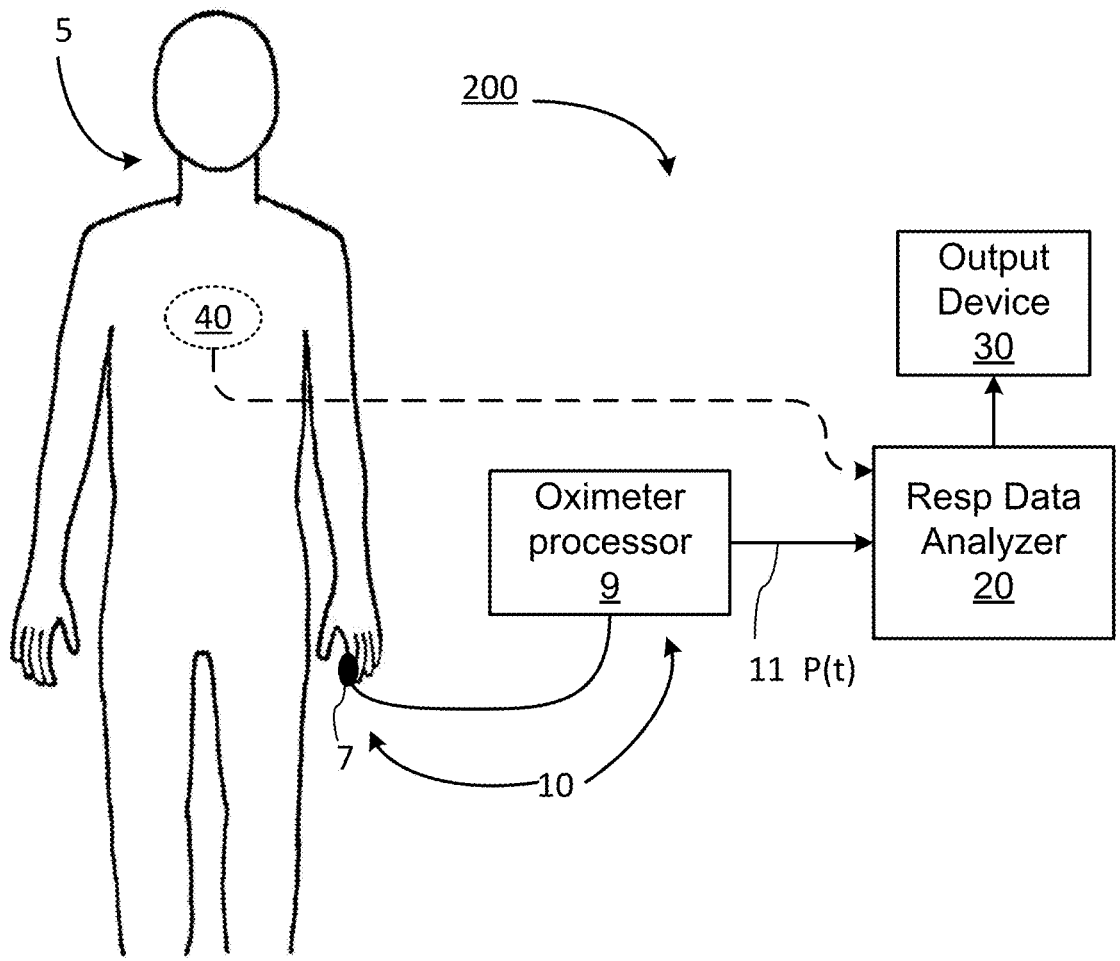
FIG. 1 is a schematic diagram of a pulse oximeter based system including an ORI computing device for assessing respiratory distress connected to a patient.

With reference to FIG. 1, there is illustrated an exemplary embodiment of apparatus 200 for assessing respiratory distress or effort in a mammalian patient 5; apparatus 200 may also be referred to herein as the respiration assessment apparatus 200 or the respiration assessment system 200. Apparatus 200 may include a plethysmograph 10, a pleth data processor (PDP) 20, and an output device (OD) 30. In some embodiments the apparatus may further include a respiration monitor 40 for monitoring patient's breathing, such as for example a spirometer or another device configured to record respiratory cycles timing as described hereinbelow. The plethysmograph 10 is preferably but not necessarily an optical plethysmograph, such as for example a pulse oximeter.

The pulse oximeter 10 may be embodied using any suitable pulse oximeter device that is commercially available or specifically designed, and which may be configured to output at least a plethysmography (pleth) signal or data that includes a pulsatile component wherein frequencies corresponding to patient's respiration are present and not completely filtered out. As an example, the pulse oximeter 10 may be embodied in the form of, or using, a wearable electronics device such as a smart watch.

Typically, the pulse oximeter 10 includes an oximeter probe 7 coupled to an oximeter signal processor 9 as known in the art. The oximeter probe 7 may be attached to a patient's body part or appendage, such as for example a finger, or an earlobe, or other site of the patient 5 overlaying an arteriolar vascular bed as known in the art. The oximeter probe 7 may be configured to deliver light from at least one light source, typically two or more, to the patient's appendage under test and to couple a portion of the light modulated by transmission through, or reflection from, the patient's tissue into one or more photodetectors (not shown). In a typical embodiment, the pulse oximeter 10 may include two light emitting diodes (LEDs), one for emitting red light and one for emitting infrared (IR) light, and at least one photodiode, with electrical circuitry configured for separately detecting the red and IR light passed through the patient's tissue. The IR light absorption is relatively unaffected by changes in arterial oxygen saturation and reflects mainly changes in blood volume, while the absorption of red light is affected both by blood volume or flow and the amount of oxygen in the blood. The electrical signals at the output of the photodetector or photodetectors are processed by the oximeter signal processor 9 to obtain two separate electrical signals $P_{Red}$ and $P_{IR}$ corresponding to the red and IR light modulated by the absorption in the patient's tissue, respectively. To that end, the oximeter signal processor 9 may include components for amplifying the electrical signal at the output of the photodetector, filtering it to reduce noise and to otherwise condition the signal, for digitizing the signal, and for demultiplexing signals related to the red and IR light to provide the two electrical signals $P_{Red}$ and $P_{IR}$ separately accounting for the absorption by the tissue of the red and IR light and for variation of the light absorption with time. The electrical signals $P_{Red}$ and $P_{IR}$ contain plethysmographic information as each of them is modulated in strength by the changes in blood flow through the patient's tissue; accordingly they may be referred to herein as the Red pleth signal and the IR pleth signal, respectively. These signals may be recorded in internal memory of the pulse oximeter and may be used by an oxygenation calculation module in the oximeter signal processor 9 to compute a parameter indicating a degree of blood oxygen saturation, such as a blood oxygenation parameter typically termed SpO2, as known in the art.

The PDP 20 connects to the oximeter signal processor 9 and is configured to obtain therefrom plethysmography data that defines a pulsatile waveform 11, which is denoted here as P(t) and which is indicative of, or includes, a pulsatile component modulated by patient's respiration. PDP 20 may also be configured to obtain from the pulse oximeter 10 the oxygen saturation data SpO2 and, optionally, a pulse rate, and may store all these data recorded over time in memory. The pulsatile waveform 11 P(t) may also be referred to herein as the first waveform 11 or the pleth waveform 11. The pleth waveform P(t) 11 may be, for example, obtained from the oximeter's IR pleth signal $P_{IR}(t)$ recorded for the patient over time. The pleth waveform signal P(t) 11 may also be obtained from the red-light related pleth signal $P_{Red}$, or a combination of $P_{Red}$ and $P_{IR}$ that includes a pulsatile component. The data defining the pleth waveform 11 P(t) may be obtained from the oximeter 10 by the PDP 20 in a digital form, or it may be digitized by the PDP 20.

The PDP 20 may be further configured to analyze the pleth waveform P(t) 11 to extract therefrom information related to a respiratory function of the patient, and to assess the presence and/or degree of respiratory distress or effort for the patient. In some embodiment, PDP 20 may be configured to generate, based on the pleth waveform 11, a measure or an indicator of a respiratory distress or effort in the patient. This measure or indicator, which generally relates to pulsus paradoxus and may be viewed also as a measure thereof, may be referred to herein as the respiratory index (RI), or as the oximetric respiratory index (ORI), in particular when it is obtained using a pleth signal measured by a pulse oximeter. In some embodiments PDP 20 may also be referred to as an ORI computing device 20 or an ORI computer 20.

Figure 2:
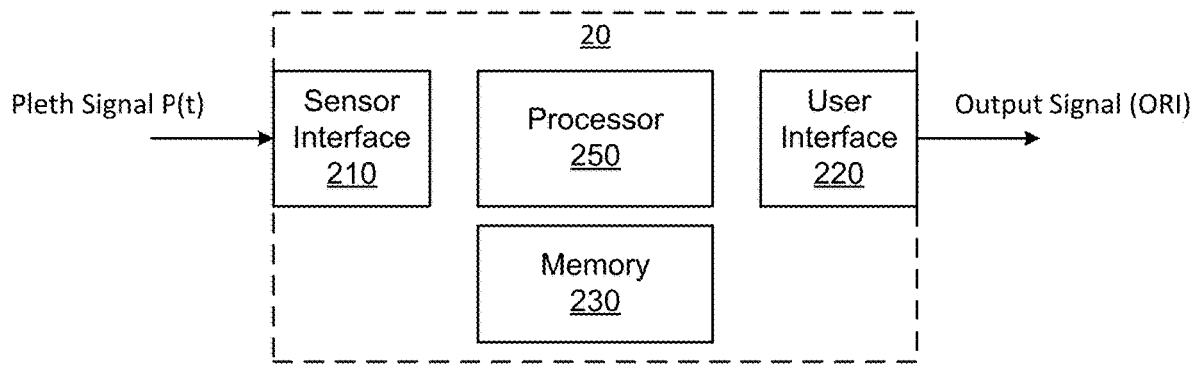
FIG. 2 is a schematic block diagram of an ORI computing device.

Referring now to FIG. 2, the PDP 20 may include a hardware processor 250, a sensor interface 210, a user interface 220, and a memory 230, for example in the form of any suitable non-volatile memory (NVM) device or a combination of a NVM and RAM. The hardware processor 250 may be, for example, any suitable microprocessor or a general purpose processor. The user interface 220 may include, for example, a graphical display, and/or a user input terminal, which may be separate from, or combined with the graphical display, such as in the form of a touch screen as known in the art. The user interface 220 may also be in the form of, or include, a network card or a computer bus interface, such as a USB interface. The sensor interface 210 is configured for connecting to the pulse oximeter 10 or another suitable plethysmograph for receiving therefrom data defining the pleth waveform 11, and may be embodied for example as a USB interface, a Bluetooth® interface, a WiFi card, or any other suitable wired or wireless interface that is configured for connecting to the pulse oximeter 10. Memory 230 may store computer instructions, executable by the processor 250, for extracting from the pleth waveform 11 information related to a respiratory function of the patient according to a method of the present disclosure whose exemplary embodiments are described hereinbelow. The computer instructions stored in memory 230 may also include instructions for computing ORI, as also described hereinbelow. It will be appreciated that PDP 20 may share components with the pulse oximeter 10, such as the processor 250 and memory 230, and may be implemented fully or partially within the same housing with the oximeter data processor 9. In other embodiment, the PDP 20 may be a separate computing device, either stationary or hand-held. In one embodiment, the PDP 20 may be implemented using a suitably configured notebook, smartphone, or tablet computer.

Exemplary embodiments of a method for assessing respiratory distress and/or effort of a mammal patient that may be implemented by the PDP 20 will now be described with reference to FIG. 1 and further with reference to FIGS. 3-16.

Figure 3:
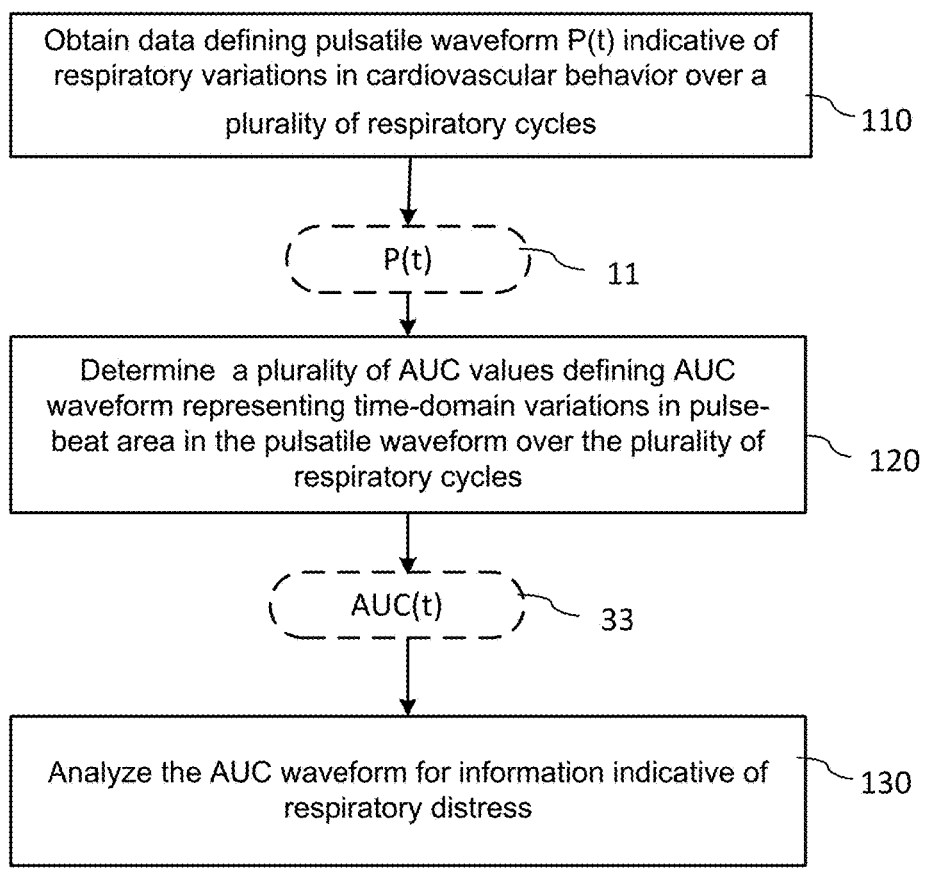
FIG. 3 is a flowchart of a method for assessing respiratory distress in a patient.

Referring first to FIG. 3, there is illustrated a flowchart of a method 100 for assessing respiratory effort or distress in a mammalian patient in accordance with one embodiment. The method 100 may start at step 110, wherein PDP 20 obtains data that define the pleth waveform P(t) 11, which extends over a plurality of respiratory cycles and is indicative of respiration related variations in pulsatile cardiovascular behavior for the patient. This data may be obtained using a suitable plethysmograph, such as the pulse oximeter 10, that is connected to the patient and records plethysmography data therefrom. The patient may be breathing freely during the measurement, or patient's breathing may be regulated with a timer to make the breathing more regular while the pleth waveform 11 is being recorded. The pleth waveform P(t) 11 obtained at step 110 is representative of a peripheral blood flow in a patient over a plurality of respiratory cycles, preferably two or more.

At step 120, PDP 20 may determine a second waveform AUC(t) 33 from the pleth waveform P(t) 11. The second waveform 33 AUC(t), which may also be referred to herein as the AUC waveform 33, may be in the form of, or defined by, a time sequence of pulse-beat area values AUC extending over the plurality of N>1 respiratory cycles; here 'AUC' stands for 'area under the curve' as described hereinbelow. In one embodiment, an AUC value may be computed for each pulse beat peak identified in the pleth waveform 11. Comparing two 'area under the curve' (AUC) values computed for two different pulse-beat peaks of a pleth signal to estimate pulsus paradoxus was described in U.S. Pat. Nos. 6,869,402, 7,044,917, and 7,828,739, which are incorporated herein by reference. In contrast, step 120 may include computing a time sequence of AUC values that is of a sufficient duration to define a waveform extending over a plurality respiratory cycles, with each respiratory cycle preferably including at least three, and preferably four or more AUC values, thereby enabling a clear identification of a respiratory signature in the resulting second waveform. The term 'time sequence" is used herein to refer to a sequence which elements are ascribed time instances, and which may be recorded as a time-ordered sequence of (time, value) pairs. A respiratory cycle is understood herein to include an inhalation followed by, or following, an exhalation by the patient. The number of respiratory cycles N in the second waveform 33 obtained at step 120 should be at least two; by way of example, N may be in the range of 3 to 20, or greater.

The second waveform 33 AUC(t) may be analyzed at step 130 for information indicative of respiratory distress or effort for the patient; this step may include analyzing the second waveform 33 AUC(t) to detect the presence or a degree of pulses paradoxus in the patient. The information obtained at step 130 may be displayed on a display device for analysis by a medical professional. In one embodiment, this step may include identifying respiratory peaks in the AUC waveform 33 related to respiratory cycles for the patient, and determining a magnitude of one or more of the respiratory peaks. In one embodiment, this step may include computing, based on the second waveform 33 AUC(t), the respiratory index RI or ORI representing a measure of respiratory effort or difficulty for the patient, as described in further detail hereinbelow. In one embodiment the respiratory index RI or ORI computed in this step represents a variation in a magnitude of the pulsatile component of the pleth waveform, and thus may also be viewed as a measure of pulsus paradoxus for the patient. Here, the magnitude of the pulsatile component of the pleth waveform may refer, for example, to an AUC for a pulse-beat peak as described in further detail hereinbelow, or a height of a pulse-beat peak in the pulsatile component of the pleth waveform, or a peak-to-valley ratio thereof, or any other similar measure of a degree of respiration-related variations in the pleth waveform.

In one embodiment, PDP 20 may be configured, for example programmed, to implement various steps of the method 100 using hardware or software logic. In one embodiment, memory 230 of PDP 20 may store instructions that are executable by the processor 250. These instructions may include, for example, instructions (a) for obtaining the pulsatile waveform 11 from the plethysmograph 10, instructions (b) for determining, from the pulsatile waveform 11, the AUC waveform 33 representing time-domain variations in pulse-beat area in the pulsatile waveform 11 over the plurality of respiratory cycles, wherein the AUC waveform 33 comprises a time sequence of pulse-beat area values extending in time over the plurality of respiratory cycles, and instructions (c) for analyzing the AUC waveform to obtain information indicative of the respiratory distress in the patient. PDP 20 may also store instructions to perform other steps of the method in various embodiment thereof as described hereinabove and hereinbelow.

Figure 4:
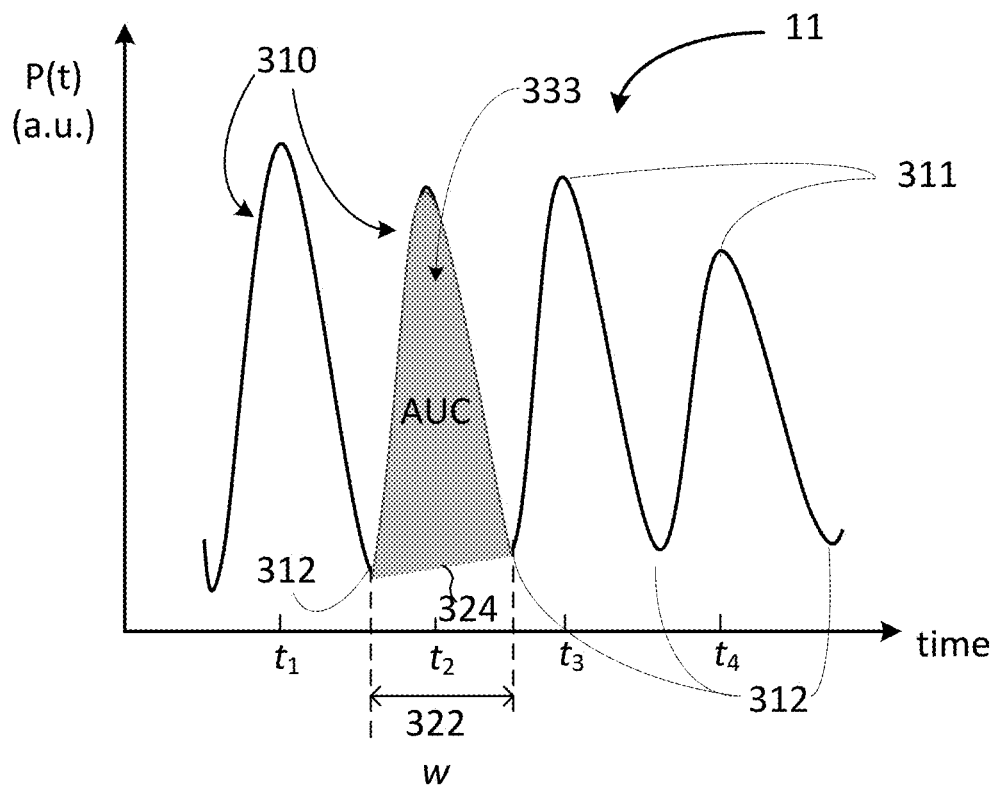
FIG. 4 is a graph schematically illustrating computing AUC values based on a pleth waveform.

The computation at step 120 of the pulse-beat area values AUC forming the second waveform 33 AUC(t) may be illustrated with reference to FIG. 4, which schematically illustrates a duration of the first (pleth) waveform 11 P(t) that includes four pulse beat periods represented by four peaks 310. The pleth waveform P(t) 11 shown in the figure reflects variations in time of the arterial blood pressure of the patient as detected by a plethysmograph, for example the pulse oximeter 10, with crests or maxima 311 of the pleth waveform 11 corresponding to systolic blood pressure of the patient, and the troughs or minima 312 corresponding to the diastolic blood pressure. Computing an AUC value 333 may involve computing or estimating an area under a portion of the pleth waveform curve P(t) corresponding to a pulse-beat peak 310, i.e. an area under the P(t) curve between two consecutive valleys or troughs 312, or a fraction thereof. In one embodiment, the AUC values 333 may be estimated by computing or estimating an area bounded from above by the curve P(t) between two consecutive troughs or valleys 312, and from below by a baseline 324 connecting the troughs or valleys 312. Exemplary approaches to computing an AUC value 333 are described in U.S. Pat. Nos. 6,869,402, 7,044, 917, and 7,828,739. By way of example, it may include detecting consecutive troughs, or minima, 312 in the pleth waveform 11, for example using a suitable peak/valley detection algorithm known in the art, and computing or estimating an integral of a portion of the first waveform 11 P(t) between each two detected consecutive troughs 312. In one embodiment, an AUC value 333 for a particular pulse-beat peak in the pleth waveform 11 may be estimated by computing a product $P_{max} \cdot w$ of a maximum P(t) value $P_{max}$ for the pulse beat and the width w 322 of the pulse beat peak, i.e. the time interval between two consecutive diastoles 312. In one embodiment this product may be scaled with a scaling coefficient f reflecting the shape of pulse-beat peak in the pleth waveform 11, i.e. $AUC \cong f \cdot P_{max} \cdot w$. In one embodiment, the first waveform P(t) 11 may be smoothed using a suitable smoothing and/or noise suppressing algorithm, such as for example a moving average, prior to computing AUC values 333.

Applying a suitable AUC computing algorithm, for example as outlined hereinabove, to the portion of the first waveform 11 illustrated in FIG. 4 will produce a sequence of four AUC values 333, one for each of the four pulse beat peaks 310 shown in the figure. These four AUC values 333 may be ascribed time instances $r_1, \ldots, t_4$ of the corresponding pulse beats represented by the peaks 310 in the pleth waveform 11 to produce a time sequence of these AUC values 333 forming a portion of the second waveform AUC(t) 33. Although FIG. 4 illustrates a relatively short portion of the pleth waveform 11 having only four pulse-beat peaks, the pleth waveform 11 obtained at step 110 preferably encompasses two or more respiratory cycles, and may typically include more than four consecutive pulse beats. In one embodiment, the number of AUC values per respiratory cycle may be estimated by the ratio $R_{heart}/R_{resp}$ of the heart rate $R_{heart}$ to the respiratory rate $R_{resp}$ for the patient, and may be, for example, in the range of 3 to 6. Accordingly, the second waveform AUC(t) 33 computed at step 120 and encompassing the N>1 respiratory cycles may include more than four, and preferably more than 6, consecutive AUC values 33. In one embodiment, the second waveform AUC(t) 33 may be stored in the form of a sequence of pairs of AUC and time values, AUC(t)={$AUC_i$, $t_i$}, i=1, . . . , M, where M>2 is the number of identified pulse beats in the first waveform 11 P(t) used for computing the second waveform 33. In one embodiment the time sequence of AUC values 333 may be smoothed to reduce noise using a suitable smoothing algorithm, such as for example by frequency-domain filtering or using a sliding average, if desired, prior to storing thereof as the AUC waveform 33.

Figure 5:
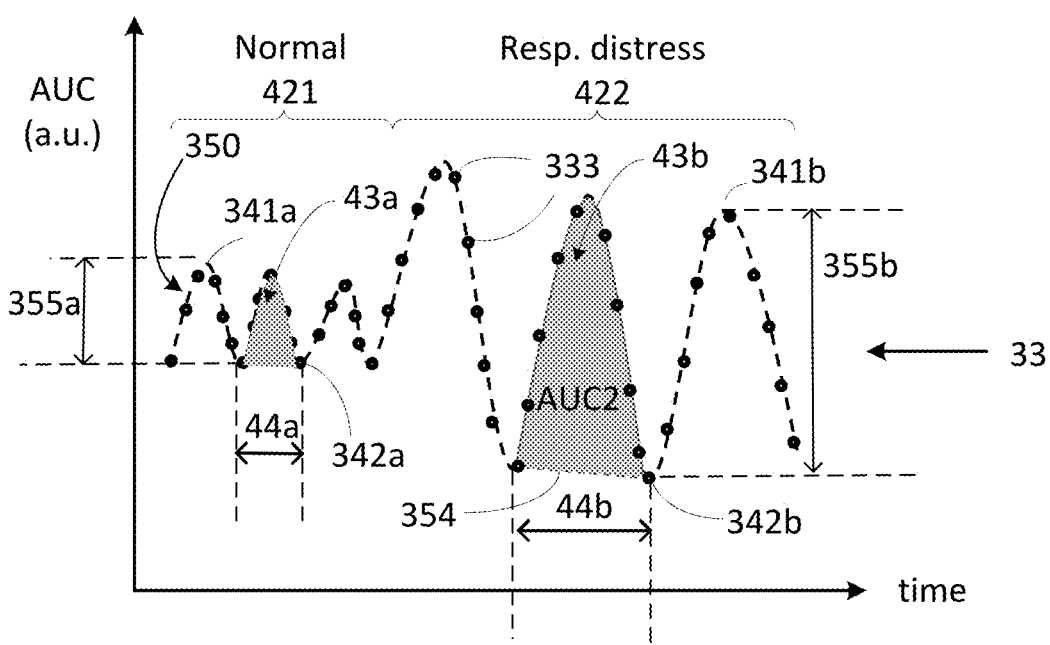
FIG. 5 is a graph schematically illustrating computing AUC2 and $R_{AUC}$ values based on an AUC waveform.

With reference to FIG. 5, there is schematically illustrated an exemplary AUC waveform 33 composed of a time sequence of AUC values 333 timed to pulse-beats in the pleth waveform 11. In the shown illustrative example, each of the plurality of AUC values 333 forming the second waveform 33 is represented as a black dot plotted at the time of the respective pulse-beat $t_i$ along the horizontal axis. Similarly to the first waveform P(t) 11, the second waveform AUC(t) 33 is oscillatory and includes a sequence of peaks 350; these peaks relate to respiratory cycles of the patient and may be referred to herein as the respiratory AUC peaks 350 or AUC peaks 350. In the shown example the second waveform 33 spans six respiratory cycles represented by the respiratory peaks 350, and includes more than 30 AUC values 333. This waveform may be analyzed at step 130 of method 100 to identify respiratory cycles and respiratory events, and to determine various respiration-related parameters for the patient, for example respiratory rate and a measure of respiratory effort or difficulty, as described hereinbelow.

The example AUC waveform 33 shown in FIG. 5 schematically illustrates changes that may occur in an AUC waveform when breathing conditions changes. Under normal breathing conditions, inhalation causes a drop in the AUC and expiration causes a rise, which results in a periodic or quasi-periodic AUC waveform that follows the respiration cycles with a relatively small amplitude of oscillations; in FIG. 5 a portion of the example second waveform 33 corresponding to normal breathing conditions is indicated at 421, wherein respiratory peaks 350, defined by crests 341a and troughs or valleys 342a, have a relatively small height 355a. The magnitude of the respiration-related oscillations in the second waveform AUC(t) 33 varies in dependence on respiratory effort, increasing when the respiratory effort or distress rises (pulsus paradoxus), and decreasing when the respiratory effort or distress is reduced. In FIG. 5, the portion of the second waveform 33 corresponding to an increased respiratory effort is indicated at 422, with more pronounced crests 341b and/or troughs 342b yielding larger respiratory peaks, as signified at least in part by a greater peak height 355b.

Since the AUC values 333 account for variations in the pulsatile arterial blood flow in the patient over the duration of a pulse beat cycle rather than at one time instance, they may better reflect changes in the pulsatile blood flow that occur during respiration than, for example, the systolic blood pressure alone. Furthermore, respiratory oscillations may be more clearly detectable in the AUC waveform 33, in particular when it extends over multiple respiratory cycles AUC(t) 33, than in the original pleth waveform 11 P(t), as the AUC waveform 33 does not include the higher-frequency component at the rate of the pulse-beat that is present in the first waveform P(t) 11. Accordingly, respiration-related information may be more conveniently extracted from the AUC waveform 33 than from the original pleth waveform 11, or from any pair of AUC values.

By way of example, in one embodiment the respiration rate may be measured based on the AUC waveform 33 by determining the frequency of the respiration-related oscillations in AUC(t), for example using a frequency-domain analysis of the second waveform 33 AUC(t) or a portion thereof, or by estimating the duration of a respiratory cycle 44a or 44b, for example by applying a suitable peak/valley detection algorithm to the second waveform 33 and determining the timings of crests 341a, 341b and/or troughs 342a, 342b in the second waveform AUC(t) 33. A peak/valley detection algorithm may also be used to obtain maximum AUC values AUCmax and minimum AUC values AUCmin corresponding to the crests 341a,b and troughs 342a,b in the AUC(t) waveform 33, respectively. Comparing the AUCmax and AUCmin values may provide a measure of the respiratory effort or distress for the patient, and/or a measure of pulsus paradoxus. An AUCmin value may be estimated, for example, as an average of the AUC(t) values for two consecutive troughs or valleys 342a or 342b bounding one respiration peak 350. By way of example, in one embodiment step 130 may include computing a peak-to-valley ratio $R_{AUC}$=AUCmax/AUCmin, a difference AAUC= (AUCmax−AUCmin), or another mathematical function of AUCmax and AUCmin representing their comparison. In one embodiment, the AUCmax and AUCmin values may be averaged over two or more respiratory cycles of the second waveform 33. In one embodiment, the computed function of the AUCmax and AUCmin, for example $R_{AUC}$ or ΔAUC, may be output as the respiratory index RI or ORI, or in addition to a respiratory index, which may be otherwise computed as described hereinbelow.

In one embodiment step 130 may include computing a second area under the curve value AUC2, or AUC of AUC, for one or more respiration cycles in the second waveform AUC(t) 33, once respiration cycles or peaks 350 in the second waveform 33 are identified. AUC2 values are illustrated in FIG. 5 by example shaded areas 43a and 43b, each of which defined by an area under a portion of the curve of the second waveform 33 corresponding to one respiratory cycle, and are generally referred to herein as the AUC2 values 43. In one embodiment, the AUC2 values 43 measured for the patient, or a function thereof, may be provided as an indication of the respiratory effort or distress for the patient. In one embodiment, AUC2 values 43, optionally scaled and/or averaged as desired, may be output as the respiratory index RI or ORI to indicate the degree of the respiratory effort or distress for the patient, including as a measure of pulsus paradoxus. A variety of scaling factors may be applied; for example, in one embodiment AUC2 values 43 may be scaled to account for variations in the respiratory cycle duration.

Generally, both the height 355a, 355b and the width 44a, 44b of the respiratory peaks in the AUC curve 33 may vary with time and in dependence on the respiratory effort exerted by the patient or the respiratory distress experienced by the patient. The height 355a, 355b AAUC of the respiratory peaks in the AUC(t) waveform 33, ΔAUC=(AUCmax−AUCmin), may be generally referred to herein as the respiratory peak height 355, and the width or duration 44a, 44b of the respiratory peaks 350 in the AUC(t) waveform 33 may be generally referred to herein as the respiratory peak width or duration 44. Advantageously, the AUC2 values 43 take into account not only the height 355 of the respiratory oscillations in the AUC waveform 33, but also the respiratory cycle duration 44 and the shape of the respiratory AUC peaks 350, and therefore AUC2 may be a better measure of the respiratory effort or distress by the patient than that obtained simply by comparison of the maximum and minimum values of the AUC, as was observed in patients testing both for timed and free breathing.

It will be appreciated that AUC2 values 43 may be computed for the AUC waveform 33 in the same or similar way as the AUC values 333 were computed for the pleth waveform P(t) 11. This computation may involve estimating the value of an integral $$J_1 = \int [AUC(t) - B(t)] dt, \quad (1)$$

wherein the integration is performed over the duration of the AUC waveform 33 between two consecutive troughs or minima 342a or 342b, where B(t) represents a baseline 354 that bounds the area under the AUC(t) curve 33 for the respiratory cycle from below. In one embodiment, B(t) may be set to zero, or omitted. In one embodiment, B(t) may be set to be equal to an AUC(t) value at one of the two troughs 342 bounding the respiratory cycle peak 350, or an average thereof; in one embodiment, B(t) may be set to be equal to AUCmin for the respiratory cycle peak. For example, the AUC2 value for a respiratory cycle may be computed by summing the products of AUC values 333 $AUC_i$ within the corresponding respiratory peak 350, which may be offset by a baseline, by the respective pulse bit period $\Delta t_i = (t_{i+1} - t_i)$, or by computing and optionally scaling a product of the respiratory peak height 355 and its width 44, or in any other suitable way an area under a curve may be estimated.

Figure 6:
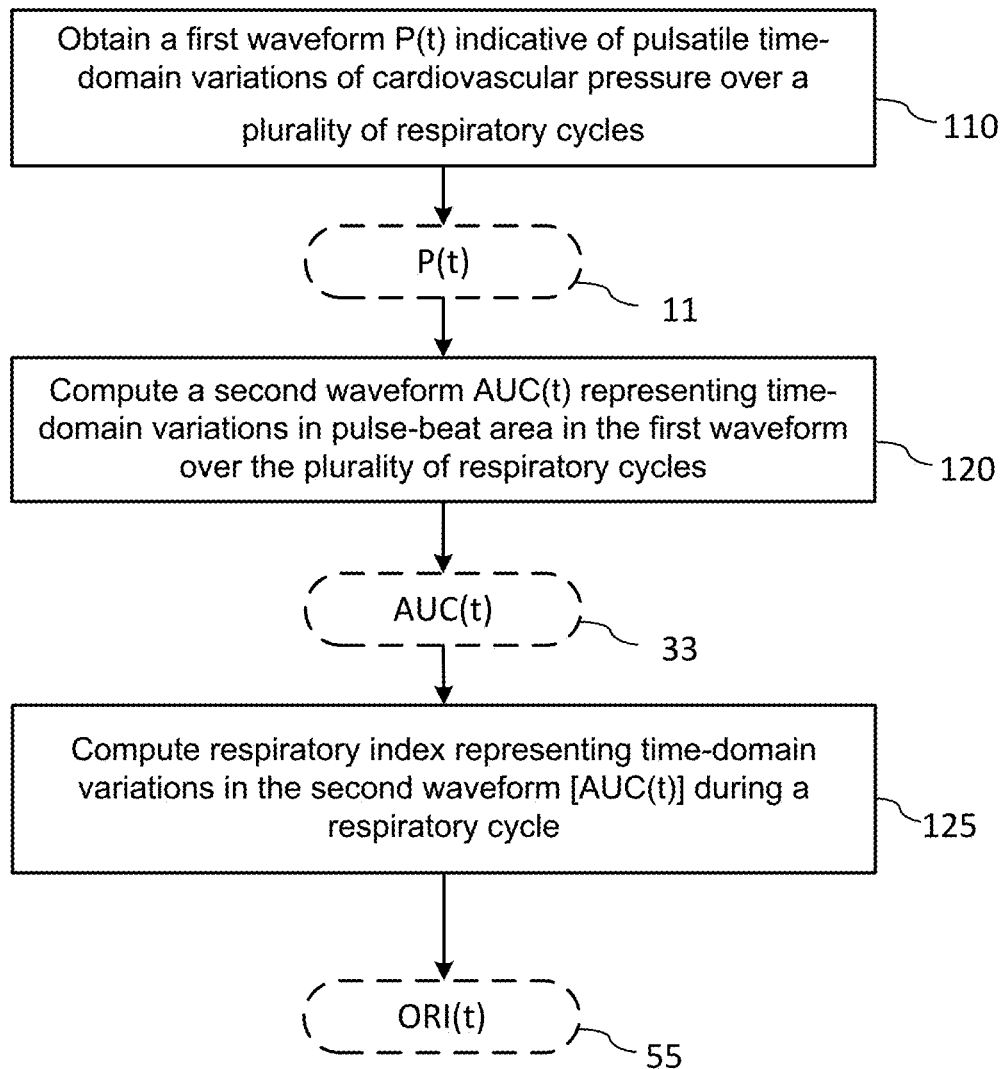
FIG. 6 is a flowchart of a method for assessing respiratory distress in a patient using ORI.

Accordingly, in one embodiment the PDP 20 may be configured, for example programmed, to implement steps or operations illustrated in FIG. 6, generally designated as method 100a. After obtaining the first (pleth) waveform P(t) 11 at step 110 and computing therefrom the second waveform AUC(t) 33 at step 120, for example as described hereinabove with reference to FIG. 3, the PDP 20 may proceed to step 125 of computing the respiratory index ORI or RI 55 representing a magnitude of time-domain variations in the second waveform 33 during a respiratory cycle. As described hereinabove, in one embodiment the ORI or RI 55 may be computed as a function representing a comparison of the maximum and minimum AUC values over a respiratory cycle or cycles, for example as a function of AAUC or $R_{AUC}$. In another embodiment, ORI may be assigned the AUC2 value 43, which may or may not be scaled for convenience of representation and/or averaged over two or more respiratory cycles or peaks 350, and which may be computed as described hereinabove with reference to FIG. 5. In one embodiment, step 125 may include identifying respiratory peaks 350 in the AUC waveform 33 prior to computing ORI. In one embodiment, the PDP 20 may output, for example display and/or save in memory, ORI values as a function of time, ORI(t), as obtained while the pleth waveform data are being collected for the patient with the pulse oximeter 10 or another suitable plethysmograph. In one embodiment, PDP 20 may be configured to generate an alarm signal when the respiratory index, or a function thereof, crosses a pre-defined threshold. The $R_{AUC}$ and in particular AUC2 were found to correlate well with respiratory effort by the patient, as described hereinbelow for two exemplary patient's test.

In some embodiments, the output of the method may be calibrated, for example by a suitably configured PDP 20, in terms of a spirometry parameter (SP), which may also be referred to as a lung function indicator, that is generally accepted in the art for a particular medical condition or test. Examples of SP include, but are not limited to, forced vital capacity (FVC), forced expiratory volume (FEV), forced expiratory flow (FEF), peak expiratory flow (PEF), or the like. FVC is a medical term referring to the volume of air that a patient can forcefully blow out after a full inspiration. FEV refers to the volume of air that a patient can forcefully blow out after a full inspiration during a set time, typically 1 second. FEF refers to the flow of air blown out of the lung during the middle portion of a forced expiration. PEF measures the maximal volumetric air flow rate achieved during the maximally forced expiration after a full inspiration, for example in liters per minute or in liters per second. The SP values such as, for example, PEF are conventionally used in the art as proxy indicators of respiratory distress for a patient, for example as an indicator of asthma severity. For example, in one embodiment internal memory 230 of the PDP 20 may store respiratory index calibration data, for example a look-up table, relating ORI or RI to a preferred spirometry parameter such as for example PEF. In one embodiment memory 230 may further store instructions for estimating an SP value, for example a FVC, FEV, or PEF, from ORI or RI using the respiratory index calibration data, and to output a value of the preferred spirometry parameter corresponding to a measured ORI or RI value according to the calibration data. In one embodiment, PDP 20 may be configured to generate an alarm signal when the SP value estimated from the ORI and RI values crosses a pre-defined threshold.

Figure 7:
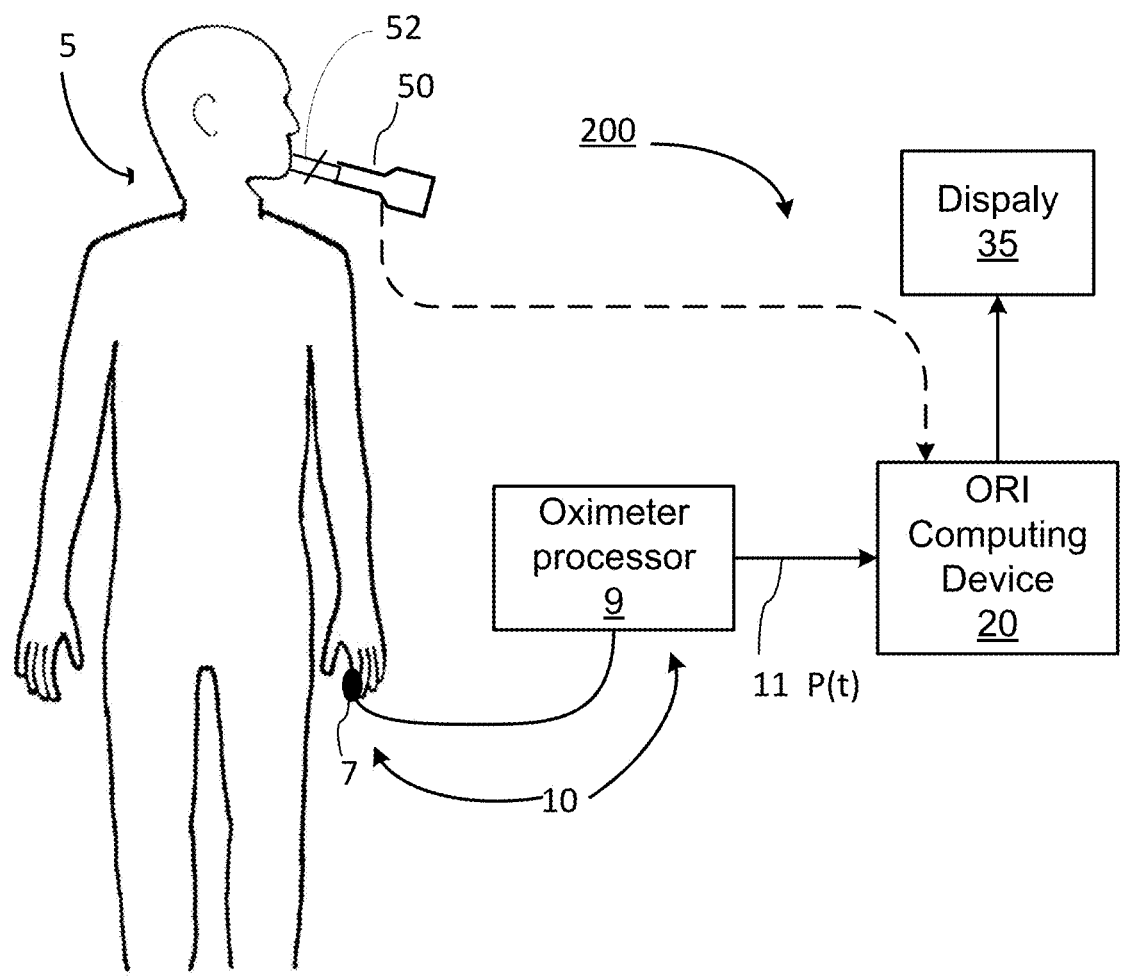
FIG. 7 is a schematic diagram illustrating calibration of the pulse oximeter based system of FIG. 1.

With reference to FIG. 7, in one embodiment the method may include a calibration step or procedure at which the patient 5 or a tester breathes through an air flow restriction device 52, such as a variable valve, and ORI or RI values for a patient as measured by the apparatus 200 are referenced to a preferred spirometry parameter SP measured by a spirometer 50. The spirometer 50 may be, for example, in the form of any suitable peak flow meter that is commercially available. In one embodiment the spirometer 50 may be in the form of an electronic device, which in one embodiment may be combined with the valve 52 and which records its measurement electronically. In one embodiment the spirometer 50 may communicate with the PDP 20 using a wireless or wireline connection, so that the SP measurements, for example FEV or PEF values for different settings of the valve opening, may be read by the PDP 20 electronically.

Figure 8:
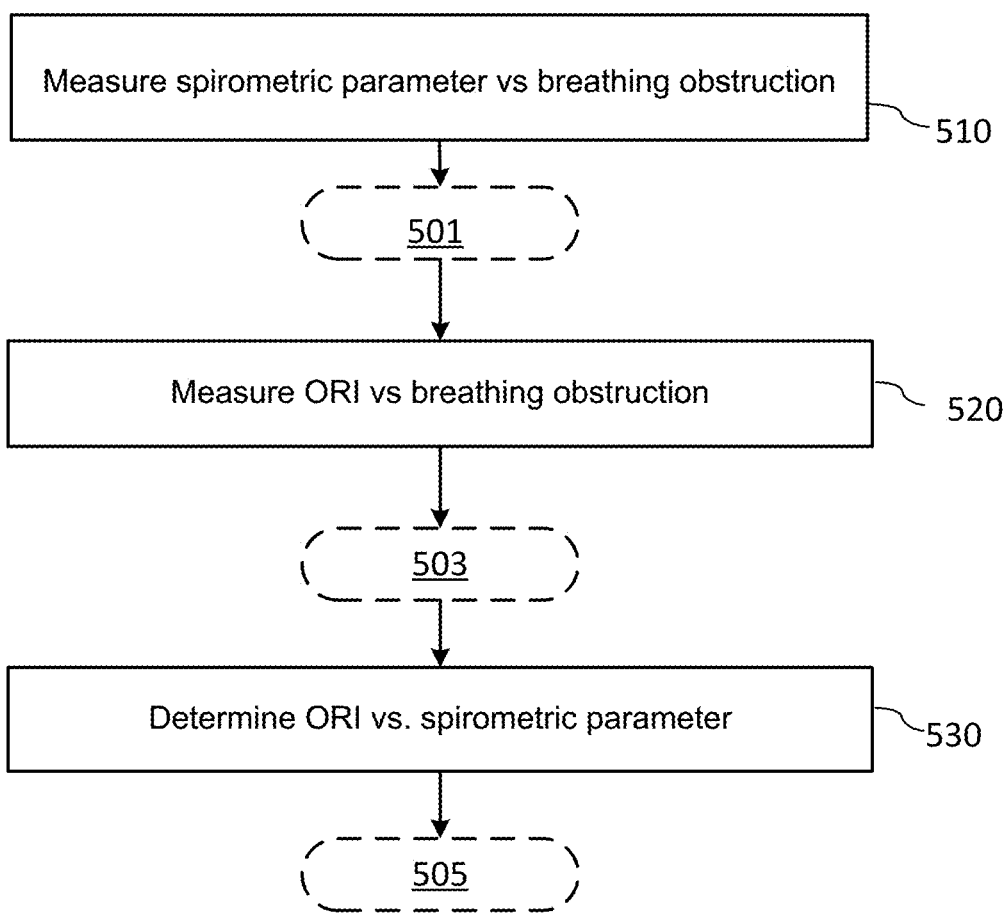
FIG. 8 is a flowchart of an example calibration procedure of the pulse oximeter based system.

Referring now also to FIG. 8, by way of example the calibration may be performed using a three-step process 500 generally illustrated by a flowchart in FIG. 8. First at step 510 a patient or a tester is asked to breathe through the valve 52 connected to the spirometer 50 while the valve opening is sequentially set to several different opening settings. For each valve setting, the patient or tester exhales as hard as they can through the valve 52, and the spirometry parameter SP from the output of the spirometer, such as for example FEV and/or PEF reading, is recorded together with the valve setting so as to obtain SP vs. obstruction data 501. Data 501 may for example include PEF values for a series of valve opening values. At step 520 the patient or tester breathes normally through the valve 52 at each setting of the valve used in step 510 while being connected to the pulse oximeter 10 of the system 20; at this step the spirometer 50 may be disconnected if desired. Normal breathing through a restriction, such as that provided by the valve 52, is an established in the art approach to simulate asthma. The pulse oximeter 10 collects data for the pleth waveform P(t) 11 over at least one respiratory cycle and preferably several, for example 3-8, respiratory cycles at each valve setting, with the ORI computer 20 using the measured pleth waveforms 11 to compute ORI for each valve setting resulting in ORI vs. obstruction data 503. At step 530 the SP vs. obstruction data 501 collected at step 510 of the calibration procedure may be combined with the ORI vs. obstruction, e.g. valve setting, data 503 obtained at step 520 to obtain ORI calibration data 505, relating ORI to PEF or a similar spirometry parameter that may be conventionally used in assessing respiratory effort or distress. The calibration data 505 may be for example in the form of a look-up table (LUT) stored in memory 230 of the PDP 20.

Figure 9:
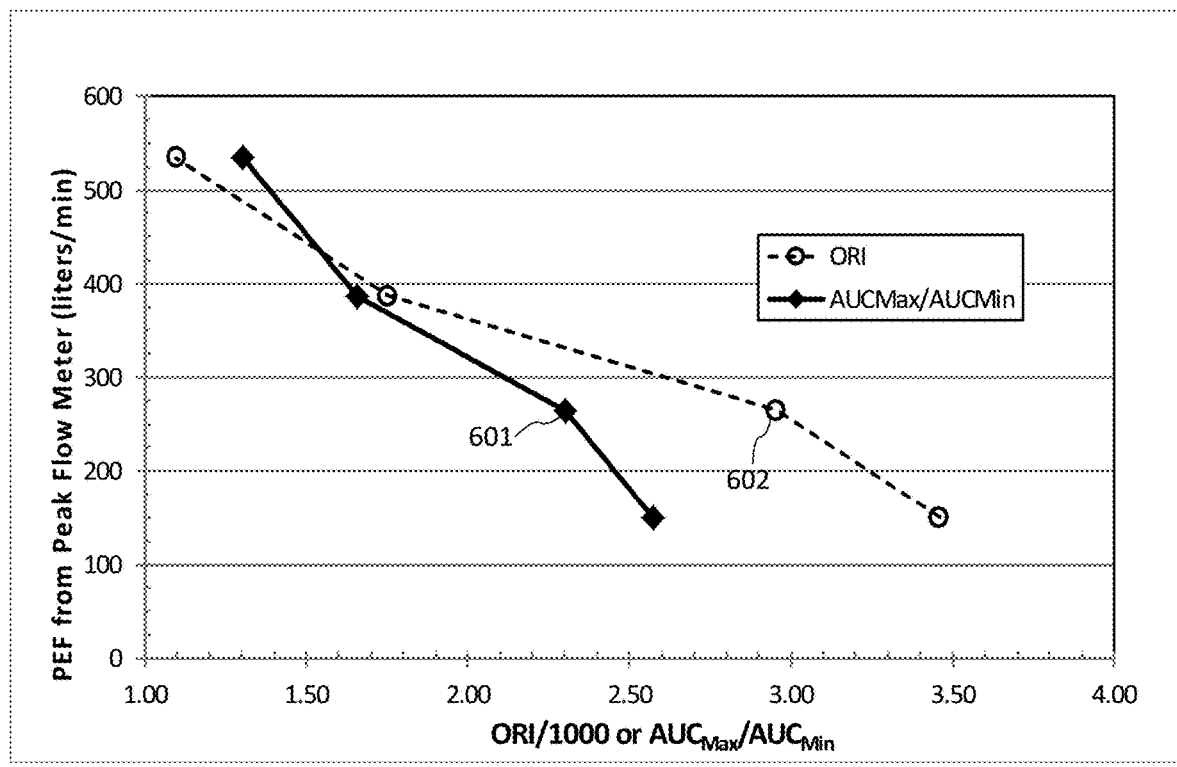
FIG. 9 is a graph illustrating a relationship between PEF and ORI measured from the IR light signal of the pulse oximeter using the calibration procedure of FIG. 8.
Figure 10:
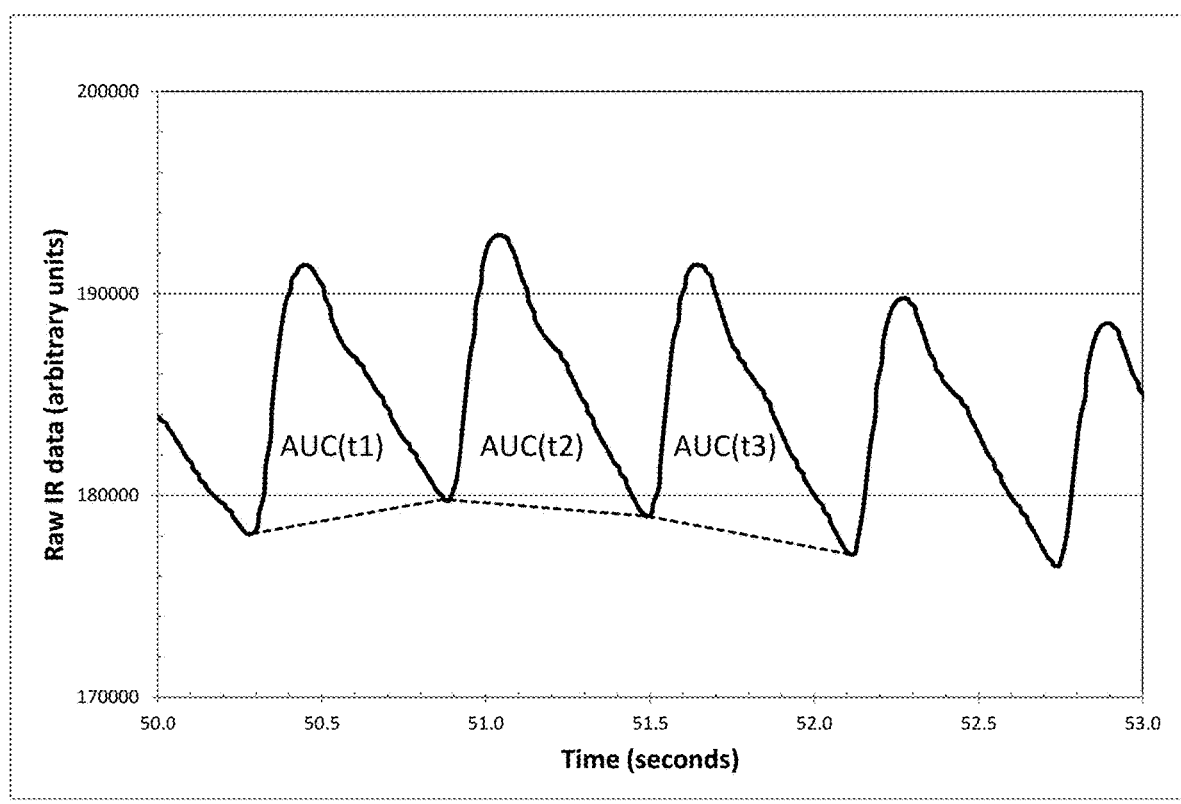
FIG. 10 is a graph showing a duration of a pleth waveform measured for the patient from the IR light signal of the pulse oximeter that was used in computing ORI values shown in FIG. 9.
Figure 11:
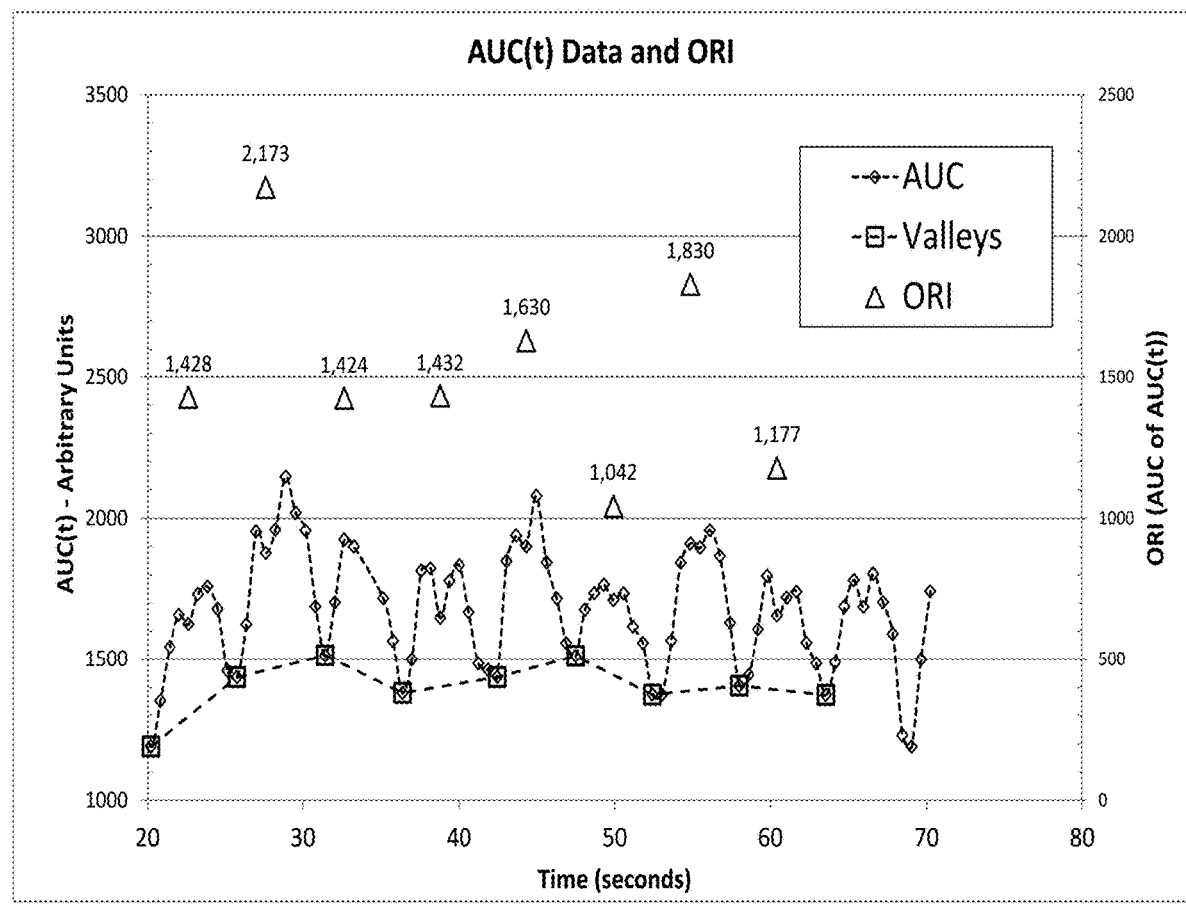
FIG. 11 is a graph showing an AUC waveform and corresponding AUC2 values computed from the pleth waveform a portion of which is shown in FIG. 10.

With reference to FIG. 9, there are illustrated exemplary ORI and $R_{AUC}$ values 602, 601 in dependence on PEF values as measured for a test patient using the aforedescribed calibration procedure and four different settings of the valve opening, with the pleth waveform 11 obtained from the IR light detection signal read from the oximeter 10. In FIG. 9 and in other examples described below with reference to FIGS. 10-14, 'ORI' refers to values obtain from AUC2 43 described hereinabove with reference to FIG. 5, unless stated otherwise. FIG. 10 illustrates a portion of the oximeter's IR pleth data that was used as the pleth waveform P(t) 11 in the AUC measurement. The pleth waveforms recorded at each valve setting at step 520 of the calibration procedure were used to compute the AUC waveform 33 AUC(t) for that valve setting. A duration of the computed AUC waveform 33 for one of the valve settings is illustrated in FIG. 11, wherein the AUC values are shown with open diamonds that are connected with dashed lines to assist in visualizing the resulting AUC waveform. The AUC waveform AUC(t) obtained for each valve settings is then processed separately as described hereinabove to obtain AUC2 and $R_{AUC}$ values for each valve setting, with the AUC2 values for each respiratory peak shown in FIG. 11 as open triangles that are positioned at time instances of corresponding AUC(t) peaks. The AUC2 value for each AUC peak was computed by numerically estimating the area bounded by the AUC curve indicated by the short-dash lines connecting adjacent diamonds, and the baseline connecting adjacent valleys in the AUC waveform as shown as the longer-dashed line in the figure. The ORI values 602 and $R_{AUC}$ values 601 in FIG. 9 for each valve setting were computed by averaging AUC2 and $R_{AUC}$ values, respectively, obtained for a plurality of respiratory peaks in the AUC waveform computed from the pleth waveform detected at that valve setting. The ORI values 602 in FIG. 9 are scaled to be on the order of $R_{AUC}$ 601 for ease of comparison.

Figure 12:
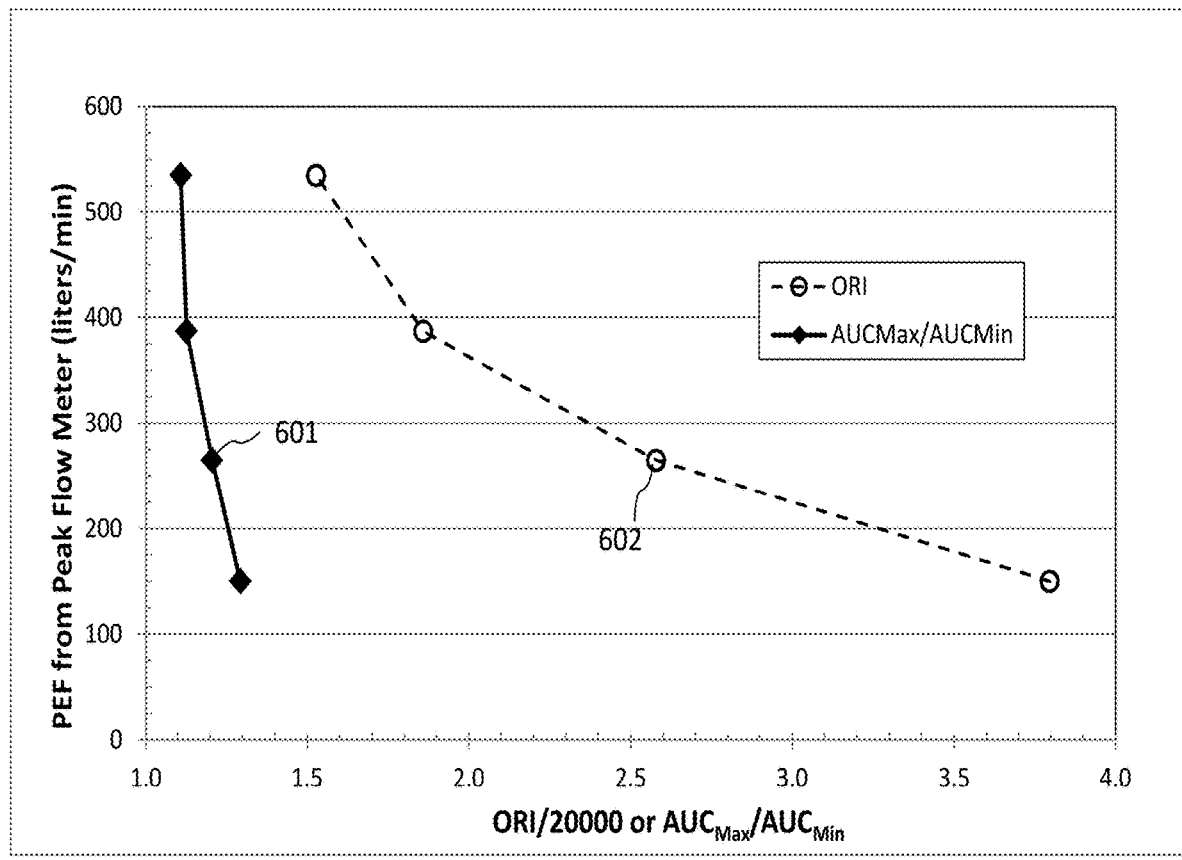
FIG. 12 is a graph illustrating a relationship between PEF and ORI measured from the IR light signal of the pulse oximeter using the calibration procedure of FIG. 8.

Data shown in FIGS. 9-11 were obtained using pleth data originating from the IR light detection, termed here the IR pleth signal, which is substantially independent on blood oxygen saturation. The oximeter signal originating from the red light detection, termed herein the Red pleth signal, generally includes a component that varies with the blood oxygen saturation, and may also be used to extract respiratory data in accordance with embodiments of the present disclosure. FIG. 12 illustrates $R_{AUC}$ and ORI values 601, 602 obtained from the Red light signal in the two-stage patient test as described hereinabove with reference to FIGS. 7-11.

It can be seen from FIGS. 9 and 12 that ORI (AUC2) values 602 and $R_{AUC}$ values 601 obtained from both Red light signal and IR light signal correlate well with the PEF values obtained for the patient at the same level of respiratory obstruction, and thus ORI computed from AUC2 and $R_{AUC}$ may both provide an indicator of breathing difficulty and/or effort and may serve as a measure of pulsus paradoxus. Furthermore, ORI computed from AUC2 appears to be more sensitive to respiratory distress/effort than $R_{AUC}$, and may thus be a better indicator of respiratory effort/distress, with the AUC2/ORI sensitivity advantage being more pronounced when the AUC2 values are obtained from the oximeter's Red light data. Indeed, for the example test data illustrated in FIGS. 9 and 12, a decrease in PEF by a factor of about 3.6 corresponds to an increase in $R_{AUC}$ by a factor of about 2 when measured from the IR light signal and only by a factor of 1.17 when measured from the Red light signal. The same decrease in PEF corresponds to an increase in ORI (AUC2) by a factor of about 3 when measured from the oximeter's IR light signal, and by a factor of about 2.5 when measured from the oximeter's Red light signal.

Timed Breathing

The pleth waveform 11 P(t) may be measured by the pulse oximeter 10 while the patient breathes freely, i.e. with the inhale/exhale timing convenient or natural for the patient, or it may be collected when the patient is asked to synchronize the inhale/exhale timing to an external timing signal; the first regime may be termed herein the free-breathing regime or simply as free breathing, while the second regime may be referred to herein as the timed breathing regime, or simply as timed breathing. Timed breathing may be conveniently used to make the patient's breathing more regular, which may simplify the detection of respiratory peaks and valleys in the AUC waveform 33.

In one embodiment, timed breathing may be used at the calibration stage to generate the calibration data 505 relating ORI to a chosen SP, such as for example PEF, for example using method 500 that is described hereinabove with reference to FIGS. 7 and 8. Referring to FIG. 7, the system 200 may include a display device 35 as the output device 30 of FIG. 1, for example in the form of a graphical display, and the system 200 may be configured to display a breathing time signal to the patient or tester at step 520, when the patient or tester breathes through the valve 52. The breathing time signal may be, for example, in the form of a bar that raises and falls in height at the desired times of inhaling and exhaling, respectively, and the patient may be asked to regulate their breathing in accordance with the rising and falling of the bar. Of course the breathing time signal may be presented to the patient or tester in a plurality of other ways, and may include, or be in the form of, an audio time signal. In one embodiment, computer-executable "breathing coach" instructions to generate the breathing time signal in a video and/or audio form may be stored in memory 230 of the PDP 20, and may be executed responsive to an input by a medical professional conducting the calibration procedure.

In some embodiments, timed breathing may be used when the patient's respiratory function is assessed using the system 200, for example as described hereinabove with reference to FIGS. 3 and 6.

Using ORI for Asthma Monitoring

In one embodiment system 200 may be used to monitor patient's respiratory functions over an extended period of time, for example overnight, or to detect changes in the patient's respiratory condition in response to a medicine. In one embodiment, ORI values generated by system 200 for the patient may be used to assess asthma severity in the patient. In one embodiment, the system may compute ORI and output, for example display, equivalent PEF or FEV values in accordance with the calibration data or LUT 505. In one embodiment, the system 200 may store in memory the AUC waveform 33 obtained during the measurement, and may display it for the viewer. Embodiments of the system 200 may also be used to assess the impact of asthma medication or treatment over time; changes in the AUC waveform 33 and/or ORI values 43 recorder over time after medicine is taken may be used to detect if the breathing effort decreases, providing a gauge of the efficacy of the medication or treatment. In one embodiment the system 200 may be configured to generate an alarm, such as a sound alarm or a blinking light alarm, when ORI exceeds a pre-defined threshold, which may indicate a severe asthma event. System 200 with an alarm configured may be used as an overnight monitor, for example for real-time monitoring of the condition of a pediatric patient by their caretakers or parents, so that they can react as soon as the alarm indicates that child's asthma becomes more severe.

Embodiments of the system and method described hereinabove, which are based on an analysis of the AUC waveform 33 measured for the patient, may also be adopted to detect, assess and/or monitor other medical conditions that affect pulmonary function of the patient, including but not limited to emphysema and sleep apnea. Sleep apnea, for example, is a condition wherein a patient, while asleep, may intermittently experience restricted airflow that may lead to complete stoppage of breathing for tens of seconds to up to 2 minutes. The restriction may occur with muscle relaxation and/or various physical changes that may occur in the patient's airway during sleep. During the airflow stoppage, the patient's blood oxygen saturation, for example as expressed in SpO2 values, may decrease significantly. Although asleep, the patient's brain will eventually wake the patient to breathe, at which time the patient may typically gasp or choke, then resume normal breathing until a next apnea event occurs. As normal breathing returns, the patient's SpO2 recovers to normal levels, with the lowest SpO2 typically seen shortly after the inhalation, or gasps, at the end of an apnea event. For a healthy patient that is awake, or when sleeping breathing normally, SpO2 is typically above 95-96%, but may drop by as much as 20-50 percentage points at the end of an apnea event. Typically, a SpO2 drop by 4 percentage points or more may indicate an apnea event.

Figure 13:
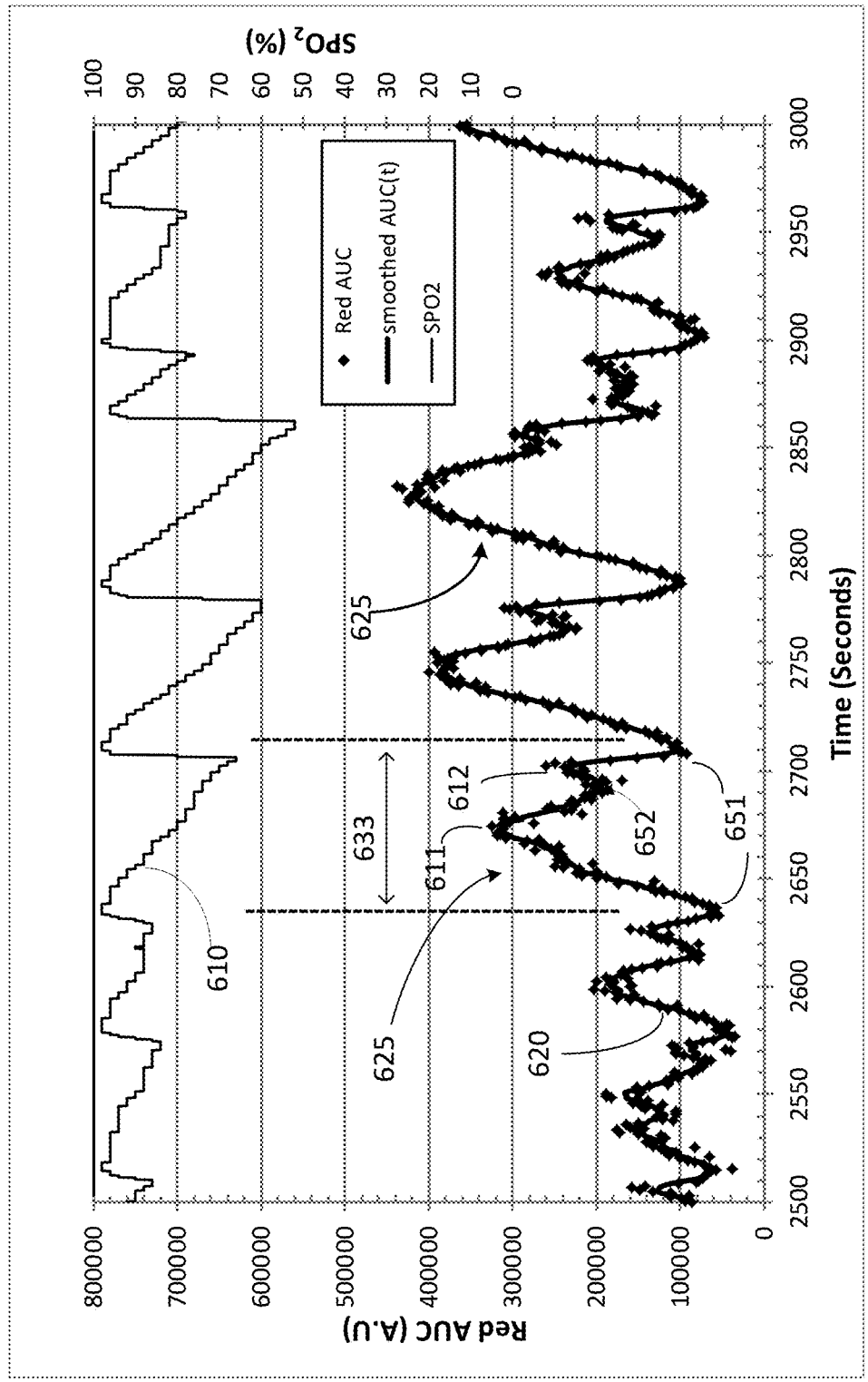
FIG. 13 is a graph showing oxygen blood saturation data (SpO2) and a duration of an AUC waveform obtained from a sleeping patient during multiple apnea events using the oximeter-based system of FIG. 1.

With reference to FIG. 13, example SpO2 measurements versus time are shown at 610, as measured by a commercial pulse oximeter for a sleeping patient suffering from sleep apnea. Eight apnea events are clearly visible from the SpO2 data 610, with SpO2 values during each apnea event gradually dropping from above 95% to below 90% and to as low as 60-50% while the patient stops breathing, followed by an abrupt rise to normal or near-normal levels after the patient finally inhales. Also shown in the same graph is a duration of an AUC waveform 620 obtained from the pulse oximeter based on a same duration of the Red light signal that was used by the oximeter to obtain the SpO2 data 610, with AUC values shown by black diamonds. The AUC waveform 620 shown by a thick black line was obtained by smoothing original AUC data, as computed from the pleth waveform, using box-car averaging with a seven-point wide sliding window. It will be appreciated that other suitable smoothing algorithms may also be used, as desired. It will also be appreciated that smoothing of the AUC data, although may be useful, may not always be required.

From comparing the AUC waveform 620 and the SpO2 waveform 610, it becomes evident that analyzing the AUC waveform 620 provides at least an alternative means to detect apnea events and assess their severity. Accordingly, the present disclosure provides a method for detecting an apnea event based on an AUC waveform, for example as may be obtained from an oximeter or another suitable plethysmograph as described hereinabove with reference to the flowcharts of FIGS. 3 and 6.

Different aspects of the AUC waveform 620 may be analyzed to detect apnea events in accordance with the method. Firstly, it is noted that the AUC waveform 620 includes abnormally wide respiratory peaks 625 that roughly correspond to apnea events evident by falloffs in the SpO2 waveform 610. Accordingly, in one embodiment of the method an apnea event may be recoded if a respiratory peak detected in the AUC waveform 620 has a width or duration 633 exceeding a pre-defined threshold, for example 30 seconds. It will be appreciated that a normal breathing cycle during apnea-free sleep is shorter that 30 seconds, and may typically be on the order of 5-15 seconds, as can be seen for example from FIG. 11. The duration of one respiratory peak 633 in the AUC waveform 620 may be determined using a peak/valley detection algorithm as known in the art of data processing. In one embodiment, the peak/valley detection algorithm may be applied to a smoothed AUC waveform wherein secondary peaks and valleys, such as a secondary peak 612 and a secondary valley 652 indicated in the figure and described hereinbelow, are smoothed out.

Another notable feature of the AUC waveform 620 is a double-hump shape of the respiratory peaks 625 corresponding to at least more pronounced apnea events, wherein a primary, relatively bigger hump or peak 611 is followed by a secondary, relatively smaller hump or peak 612, and wherein a primary valley 651 at the start of an apnea event is followed by a lesser secondary valley 652. Notably, the secondary peaks 612 may indicate the moments of time when the patient takes a breath that ends the apnea event, which is a feature that is not easily visible from the SpO2 data 610 as it takes a few seconds after the gasp for the oxygen to get into the blood and to the area of the body where the SpO2 level is being measured. Thus, the double-hump feature in the AUC waveform provides more accurate information regarding the timing of the onset of breathing after an apnea event than is available from the SpO2 data.

Accordingly, in one embodiment the apnea detection method may include detecting a double-hump structure of a respiratory peak in the AUC waveform. It will be appreciated that the detection of the double-hump respiratory peaks of the AUC waveform may be done in a plurality of ways. For example, the AUC waveform 620 may be first smoothed using a smoothing window that is sufficiently small so as to preserve the secondary valleys 652 and peaks 612, and then consecutive peaks or valleys in the smoothed AUC waveform identified and compared to detect the presence of the secondary peak 612 or valley 652 within the duration of on respiratory AUC peak 633. For example, an apnea event may be identified if a secondary peak is detected that is within a pre-defined percentage range of a preceding primary peak 611, or when a secondary valley 652 is detected that is within a pre-defined percentage range about an average AUC value for the respiratory peak duration 633. The start and end points of a respiratory peak in the AUC waveform may also be determined from the SpO2 signal, for example when SpO2 drops by more than a few percent below a pre-determined baseline.

In one embodiment the apnea detection method may include recording ORI values for the AUC waveform 620 during sleep and comparing them to a pre-defined threshold or thresholds. The ORI may be determined for each newly identified respiratory peak 625 on the basis of an AUC2 value computed for the peak, for example as described hereinabove with reference to FIGS. 5 and 11. In one embodiment, a baseline ORI value and/or a baseline AUC peak value AUCmax may be recorded during apnea-free sleep or during the patient's awake state at the start of a test prior to a patient falling asleep. The absence of apnea events may be verified, for example, by comparing SpO2 values to a baseline SpO2; by way of example, times when SpO2 exceed 96% or a similar level may be identified as apnea-free. Normal, apnea-free sleep may also be identified based on the respiration cycle duration not exceeding a pre-defined threshold, for example less than 20-30 seconds.

Figure 14:
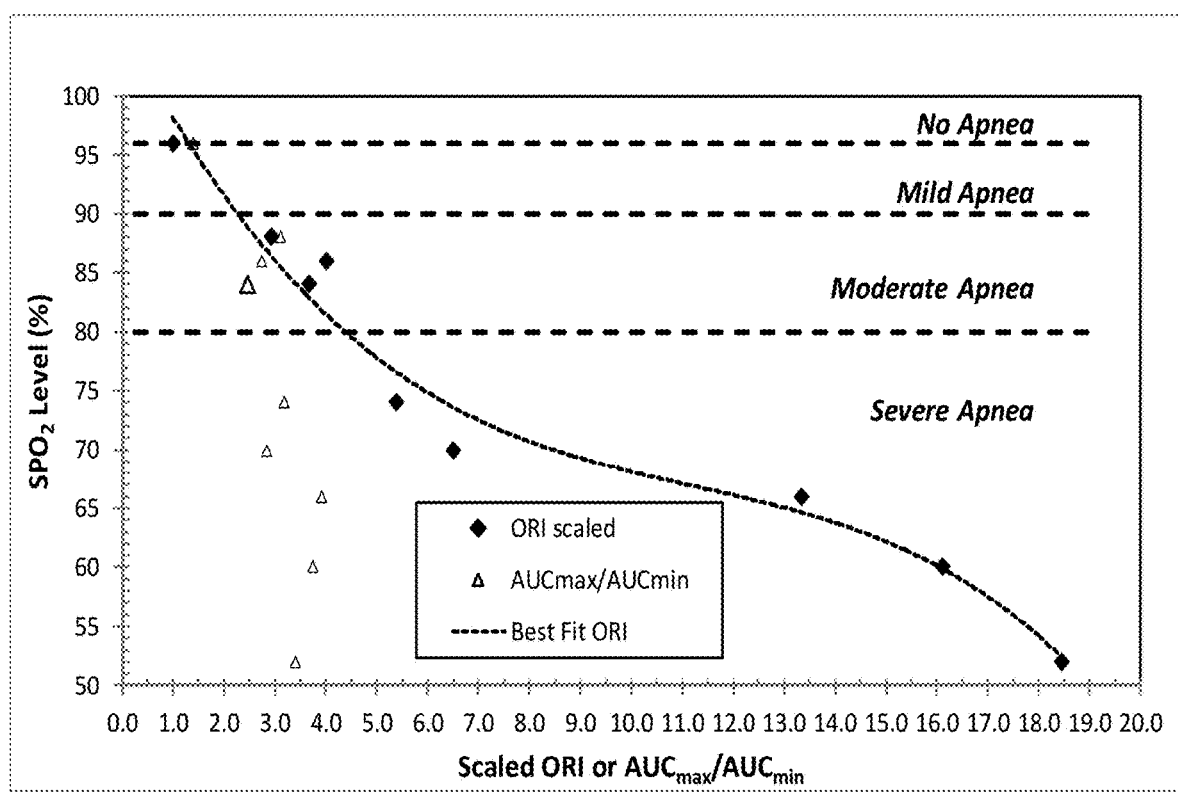
FIG. 14 is a graph showing the relationship between ORI computed from the AUC waveform of FIG. 13 and SpO2 for multiple apnea events.

FIG. 14 shows a relationship between ORI computed from AUC2 values as described hereinabove, and SpO2. The data used in this graph was obtained as described hereinabove from a sleeping patient suffering from apnea; the patient was connected to a pulse oximeter during sleep, and the oximeter's Red light signal and SpO2 readings were recorded. The oximeter's Red light signal was then used as the pleth signal to compute the AUC waveform, a portion of which is shown in FIG. 13. Each black diamond in FIG. 14 represents a respiratory event corresponding to a respiratory peak 625 in the AUC waveform, with the y-coordinate given by the minimum SpO2 oximeter reading during the respiratory event, and the x-coordinate given by ORI computed as scaled area under the curve AUC2 for the corresponding respiratory peak 625 in the AUC waveform. It can be seen that the so computed ORI values strongly correlate with the SpO2 values, and may thus be used as apnea indicators. The horizontal dashed lines in the figure exemplify thresholds for grading the severity of an apnea event based on SpO2 values. The first ORI data point in FIG. 14 at 96% oxygen saturation corresponds to a respiratory event during a non-apnea sleep in the patient; as the patient continued sleeping, apnea developed at various levels of severity, and the corresponding ORI increased with apnea severity. Intersections of a best-fit ORI(SpO2) curve shown with a dotted line in the figure may provide ORI threshold values for various apnea severity levels. In one embodiment, ORI vs. SpO2 data collected for one or more patients may be used to determine the ORI thresholds related to apnea severity, and/or a look-up table related ORI values to SpO2 values. Open triangles shown in FIG. 14 represent the same respiratory events but with x-coordinates expressed in terms of $R_{AUC}$ values computed for the respective events; it can be seen that $R_{AUC}$ values scale poorly with SpO2 and thus may not be a preferred indicator of apnea severity.

Embodiments described hereinabove analyze an AUC waveform 33 or 620 for a respiratory signature in order to detect and possibly assess respiratory distress in a patient; the respiratory signature being analyzed generally relates to pulsus paradoxus and includes respiratory peaks that correlate with respiratory cycles in the patient, with a magnitude of the respiratory peaks in the AUC waveform, expressed for example in terms of area under the curve or in term of a peak height and/or width, indicating a degree of respiratory distress. Further investigations however revealed that a phase relationship between patient's breathing cycles and the respiratory peaks in the AUC waveform may also be sensitive to respiratory distress or effort and therefore may also be used as an indicator thereof.

Figure 15:
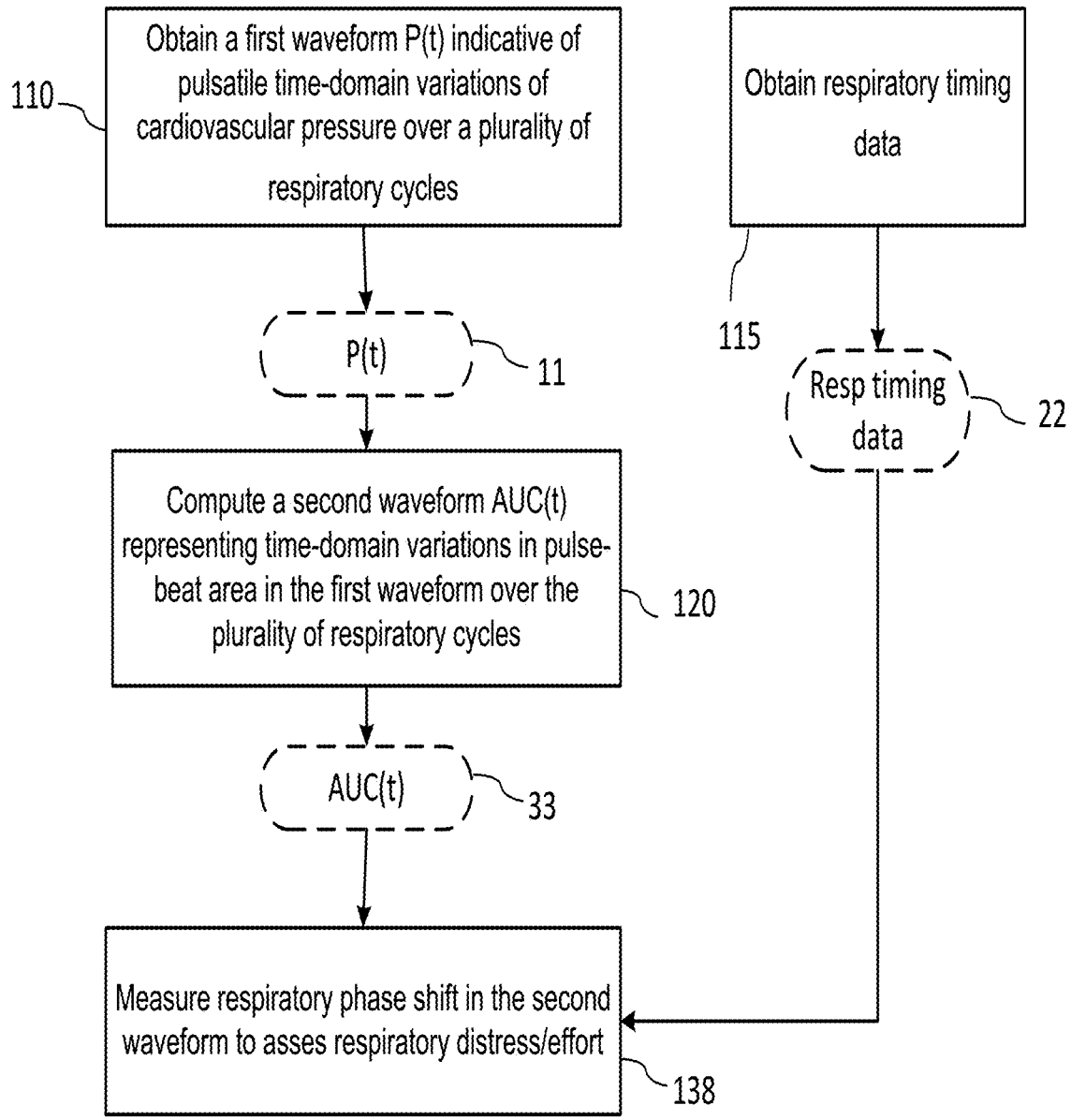
FIG. 15 is a flowchart of a method for assessing respiratory distress in a patient using a respiratory phase shift.

With reference to FIG. 15, there is illustrated a flowchart of an embodiment of the method of the present disclosure, generally indicated at 100b, which uses independent monitoring of the respiratory cycles of the patient for assessing respiratory distress or respiratory effort in the patient. The method in this embodiment may include step 115 of obtaining respiratory timing data 22 from the respiratory timing monitor 40 coupled to the patient. The respiratory timing data 22 should be obtained concurrently with but independently from obtaining the first (pleth) waveform P(t) 11 at step 110 as described hereinabove with reference to FIGS. 3 and 6. The respiratory timing data 22 includes data indicating the timing of inspiration, or inhaling, and expiration, or exhaling, by the patient. After the second waveform AUC(t) 33 is computed from the first waveform P(t) 11 at step 120 as described hereinabove, it may be time-synchronized with the respiratory timing data 22 to establish a common time scale. This can be done automatically on a hardware level, for example if the respiration monitor 40 and the pulse oximeter 10 use a common clock signal, or it can be done in software, for example by synchronizing to a common event. At step 138, the second waveform AUC(t) 33 may be correlated with the respiratory timing data 22 to detect and/or measure a phase shift $\phi$ between the respiratory crests 341 or troughs 342 in the AUC(t) waveform 33 and the timing of inhalation and exhalation by the patient, which may be termed a respiratory phase shift. In this embodiment, the method takes advantage of an observation that respiratory oscillations in the AUC waveform 33 shift with respect to the timing of inhalation and exhalation by the patient.

This observed effect is schematically illustrated in FIGS. 16A-16C, where respiration-related rises and falls of the second waveform AUC(t) 33 are shown relative to periods of inhaling and exhaling by the patient. For normal non-obstructed breathing, rising edges of the respiratory peaks in the AUC(t) curve 33 tend to occurred when the patient exhales, while falling edges of the respiratory peaks in the AUC(t) curve 33 tend to coincide in time with inhaling by the patient, as schematically illustrated in FIG. 16A. In a condition of severely obstructed breathing, the respiratory oscillations in the AUC waveform may shift in phase by about 180°, so that the rising edges of the respiratory peaks in the AUC(t) curve 33 may coincide in time with inhaling by the patient, while falling edges of the respiratory peaks in the AUC waveform correlate with exhaling by the patient, as schematically illustrated in FIG. 16C. In an intermediate condition of moderately obstructed breathing the respiratory oscillations in the AUC waveform may shift in phase by about 90°, as schematically illustrated in FIG. 16B. Therefore, the respiratory phase shift $\phi$ may provide another indication of respiratory distress and/or effort, and may be measured or estimated at step 138 of the method for that purpose. Referring back to FIG. 5, this phase shift may be estimated, for example, by determining positions of the troughs 342 and/or crests 341 of the respiratory oscillations in the AUC waveform 33 with respect to the timing of the inhaling and/or exhaling by the patient. The respiration monitor 40 that is capable of providing the respiration timing data may be embodied in a variety of ways; for example it may be in the form of a spirometer, or it may be embodied using a portable computing device, such as a smart phone that includes an accelerometer and is capable of recording accelerometer data, that is positioned at the patient's chest and moves therewith as the patient breathes.

Referring back to FIG. 4, the computation of the AUC values 333 may be conditioned on identification of pulsatile oscillations in the pleth waveform P(t) 11. However, the pleth signal may fluctuate not only due to the variations in the peripheral blood flow in the patient's appendage to which the oximeter sensor is connected, but also due to other events such as for example sudden movements by the patient. Such events may result in sudden spikes in the pleth waveform. In one embodiment, the AUC(t) computation in step 120 of method 100, 100a, or 100b may be configured to identify such events in the pleth waveform P(t) 11 and exclude them from computing the AUC values 333. By way of example, all P(t) values that cross a threshold may be excluded. The threshold may be pre-defined or it may be dynamically defined based on preceding P(t) data, for example when a P(t) value exceeds an average of a several preceding pulsatile maxima in the pleth waveform 11 by more than a pre-defined offset, or when a P(t) value is below an average of a several preceding pulsatile minima in the pleth waveform 11 by more than a pre-defined offset.

Embodiments described hereinabove may be advantageously used for assessing respiratory distress and/or effort that accompanies a variety of medical conditions, including but not limited to asthma, emphysema, and sleep apnea, and measuring pulsus paradoxus. By analyzing an AUC waveform that extends over a plurality of breathing cycles, the respiratory signature in the original pleth signal may be more reliably identified, and pulsus paradoxus more reliably measured than by comparing two AUC values as described in the prior art. Noise and external influences affecting the measured pleth waveform, such as sudden movements by the patient, do not typically have the regularity of breathing cycles of a mammal, and thus may be separated from the respiratory signature by operating with a time sequence of AUC values that extends over several respiratory cycles. AUC2 values, or AUC of AUC, account for changes that occur in the pulsatile pleth signal during a duration of the respiratory cycle, or during at least a significant portion thereof preferably encompassing more than two pulse beats, including changes in the pulse and respiration rates, and thus may contain more information about respiratory function of the patient than may be obtained simply by comparison two AUC values. Furthermore, embodiments of the present disclosure provide a new measure of the respiratory distress or effort, termed herein RI (respiration index) or ORI (oximeter respiration index), that may be obtained based on reading from a conventional pulse oximeter, for example, and which is shown to correlate well with conventional measures of respiratory distress for various medical conditions, such as but not limited to PEF for asthma and related conditions, and SpO2 for sleep apnea, some of which may be more difficult to monitor.

It will be appreciated by those skilled in the art that block diagrams herein can represent conceptual views of illustrative circuitry embodying the principles of the technology. Similarly, it will be appreciated that any flow charts, state transition diagrams, pseudocode, and the like represent various processes which may be substantially represented in computer readable medium and so executed by a computer or processor, whether or not such computer or processor is explicitly shown. The functions of the various elements including functional blocks labeled or described as "processors" or "controllers" may be provided through the use of dedicated hardware as well as hardware capable of executing software in association with appropriate software. When provided by a processor, the functions may be provided by a single dedicated processor, by a single shared processor, or by a plurality of individual processors, some of which may be shared or distributed. Moreover, explicit use of the term "processor" or "controller" should not be construed to refer exclusively to hardware capable of executing software, and may include, without limitation, digital signal processor (DSP) hardware, read only memory (ROM) for storing software, random access memory (RAM), and non-volatile storage. Furthermore, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The above-described exemplary embodiments are intended to be illustrative in all respects, rather than restrictive, of the present invention. Thus the present invention is capable of many variations in detailed implementation that can be derived from the description contained herein by a person skilled in the art. For example, although particular embodiments described herein may have been described with reference to pulse oximeters, it will be appreciated that other types of plethysmographs, including but not limited to optical plethysmographs may also be used as the source of plethysmography data. In another example, methods used for computing AUC, AUCmin, AUCmax, AUC2, ORI, etc. that are described hereinabove with reference to one embodiment may also be used in other embodiments, and methods described hereinabove with reference to computing ORI may also be used for computing a respiratory index (RI) in embodiments wherein measurements on the patient is performed by a device other than pulse oximeter. All such variations and modifications are considered to be within the scope and spirit of the present invention as defined by the following claims. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes.

We claim:

1. A method for a pulse oximeter system comprising a user-wearable probe and a computing device configured to communicate with the probe, the probe configured to generate oximetry signals modulated by peripheral blood flow variations in a user wearing the probe, the computing device configured to process the oximetry signals collected from the probe over time to extract a pulsatile waveform, and to generate an oximetric respiratory index (ORI) value quantifying respiration-induced changes in the pulsatile waveform, the method comprising:

generating calibration data relating the ORI to a spirometric lung function parameter using an oximeter and a variable airflow restriction device; and configuring the computing device to estimate the spirometric lung function parameter for the user based on the calibration data and the oximetry signal obtained from the user-wearable probe, such as to enable the computing device to display estimated values of the spirometric lung function parameter for the user.

2. The method of claim 1 wherein the generating calibration data comprises:
   measuring by a spirometer a lung function of the user breathing through the variable airflow restriction device while the variable air flow restriction device is sequenced through a plurality of airflow restriction settings;
   acquiring, by the pulse oximeter system or a different pulse oximeter, oximetry signals for the user breathing through the variable airflow restriction device while the variable airflow restriction device is sequentially set to at least some of the airflow restriction settings; and
   relating, by a digital processor, the measurements of the lung function to ORI values obtained from the acquired oximetry signals corresponding to same ones of the airflow restriction settings.

3. The method of claim 1 comprising:
   computing by the computing device an oscillatory area-under-curve (AUC) waveform extending over a plurality of respiratory cycles of the user, the oscillatory AUC waveform comprising at least three first AUC values per respiratory cycle, wherein the at least three first AUC values represent respective pulse-beat areas of at least three different pulse beats in the pulsatile waveform;
   identifying, by the computing device, one or more respiratory peaks in the AUC waveform, and
   computing the oximetric respiratory index based on at least one of a magnitude and a duration of at least one of the one or more respiratory peaks in the AUC waveform.

4. The method of claim 3, wherein computing the respiratory index comprises computing one or more second AUC values for the one or more respiratory peaks in the AUC waveform, each second AUC value representing an area-under-curve of one of the one or more respiratory peaks in the AUC waveform.

5. The method of claim 3 comprising displaying the oximetric respiratory index on a display device as a function of time.

6. The method of claim 2 comprising using a video or audio output device to generate, while the oximetry signals for the user are being acquired, a timing signal for the user to regulate user's breathing.

7. The method of claim 1, wherein the spirometric lung function is one of a forced vital capacity (FVC), forced expiratory volume (FEV), or peak expiratory flow (PEF).

8. The method of claim 1 wherein the user-wearable probe is implemented with a smart watch.

9. The method of claim 8 wherein the computing device is comprised in at least one of: the smart watch, a smartphone, and a tablet computer.

10. The method of claim 3, wherein the computing device is configured to perform operations comprising:
    receiving respiratory timing data for the user, the respiratory timing data being obtained concurrently with the oximetry signals and using a respiratory timing monitor; and,
    electronically processing the respiratory timing data and the oximetry signals to compute a phase shift between one or more respiratory cycles in the AUC waveform and corresponding one or more respiratory cycles in the respiratory timing data to evaluate respiratory effort or respiratory distress in the user.

* * * * *